United States Patent
Abe et al.

(10) Patent No.: US 6,534,766 B2
(45) Date of Patent: Mar. 18, 2003

(54) CHARGED PARTICLE BEAM SYSTEM AND PATTERN SLANT OBSERVING METHOD

(75) Inventors: Hideaki Abe, Yokohama (JP); Yuichiro Yamazaki, Tokyo-To (JP); Kazuyoshi Sugihara, Kanagawa-Ken (JP); Masahiro Inoue, Zama (JP)

(73) Assignees: Kabushiki Kaisha Toshiba, Kawasaki (JP); Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/816,468

(22) Filed: Mar. 26, 2001

(65) Prior Publication Data

US 2001/0025925 A1 Oct. 4, 2001

(30) Foreign Application Priority Data

Mar. 28, 2000 (JP) .......................................... 2000-089909

(51) Int. Cl.$^7$ ............................................... H01J 37/26
(52) U.S. Cl. .................... 250/307; 250/310; 250/396 R; 250/396 ML
(58) Field of Search ............................... 250/307, 310, 250/396 R, 396 ML

(56) References Cited

U.S. PATENT DOCUMENTS 5,023,453 A * 6/1991 Adachi et al. ............... 250/309
5,894,124 A * 4/1999 Iwabuchi et al. ........... 250/310
6,039,000 A * 3/2000 Libby et al. ............. 118/723 E
6,114,695 A * 9/2000 Todokoro et al. ........... 250/310

FOREIGN PATENT DOCUMENTS

JP          8-255588          10/1996

OTHER PUBLICATIONS

US 2002/0050565 A1, Tokuda et al. USPTO publication of May 2, 2002.*

* cited by examiner

Primary Examiner—Bruce Anderson
Assistant Examiner—Zia R. Hashmi
(74) Attorney, Agent, or Firm—Finnegan, Henderson, Farabow, Garrett & Dunner, L.L.P.

(57) ABSTRACT

A charged particle beam system comprising a charged beam source, a condenser lens, a scanning deflecting device, an objective lens and a secondary electron detector further comprises a slant observing deflecting device arranged between the objective lens and a sample. The slant observing deflecting device deflects charged particle beams immediately before the surface of the sample, to cause the charged particle beams to be slantingly incident on the sample. The deflection angle of the charged particle beams is controlled by a DC current component which is inputted to the slant observing deflecting device. The irradiation position shift of the charged particle beams due to the slant deflection is corrected and controlled by feeding an input value of the slant observing deflecting device and the slant angle of the charged particle beams back to the input value of the scanning deflecting device.

23 Claims, 14 Drawing Sheets

CHARGED PARTICLE BEAM SYSTEM AND PATTERN SLANT OBSERVING METHOD

CROSS REFERENCE TO RELATED APPLICATION

This application claims benefit of priority under 35USC §119 to Japanese patent application No. 2000-089909, filed on Mar. 28, 2000, the contents of which are incorporated by reference herein.

BACKGROUND OF THE INVENTION

1. Field of the Invention

The present invention relates generally to a charged particle beam system. More specifically, the invention relates to observation, inspection and measurement using charged particle beams.

2. Description of the Prior Art

A typical process for producing a semiconductor device includes a step of measuring the dimension of a pattern which is formed on a substrate such as a wafer or a reticle. In the measurement of the dimension of such a pattern, a critical dimension measurement SEM (Scanning Electron Microscope) having a length measuring function is usually used for acquiring a top-down image of the pattern to measure pattern widths, hole diameters and so forth in the top-down image.

In recent years, three-dimensional information such as the shape of the sidewall of a pattern, not only such two-dimensional information, is being an important evaluated item in an actual producing process. Conventionally, a cross-section SEM, a review SEM or the like is used for obtaining the three-dimensional information of a pattern.

However, the cross-section SEM takes a lot of time to carry out processing, since a sample must be broken into minute pieces and be mounted on a predetermined jig. In addition, the cross-section SEM is not suitable for an in-line evaluation for carrying out an evaluation in a producing process, since it is a destructive inspection.

On the other hand, the review SEM is a system for causing electron beams to be obliquely incident on a sample to observe the three-dimensional shape of a pattern by slanting a sample table of a scanning electron microscope together with a transporting mechanism. The review SEM is more suitable for an in-line evaluation than the cross-section SEM, since it is not required to process the sample.

However, the motion of the review SEM is slow since the sample table and a stage are mechanically slanted. In addition, since the review SEM is a separate system from the above-described critical dimension measurement SEM, there is the possibility that the number of producing steps may increase. In order to solve this problem, it is considered that a tilted stage is mounted on the critical dimension measurement SEM. However, it is required to provide a complicated stage mechanism in order to slant a sample table, so that there are problems in that the size of the system increases and the positioning accuracy of the stage deteriorates. For that reason, it is difficult to mount the tilted stage on the critical dimension measurement SEM in the present circumstances.

SUMMARY OF THE INVENTION

It is therefore an object of the present invention to eliminate the aforementioned problems and to provide a charged particle beam system and a pattern slant observing method, which can be used for carrying out an in-line evaluation and which have a rapid, high-accuracy slant observing function.

According to the first aspect of the invention, there is provided a charged particle beam system comprising:

a charged particle beam emitting device for generating charged particle beam and for irradiating a sample to be inspected with the charged particle beam; a condenser lens for condensing the charged particle beam; a scanning deflecting device for deflecting the charged particle beam to scan the charged particle beam on the sample; an objective lens for focusing the charged particle beam on the surface of the sample; a slant observing deflecting device, arranged between the objective lens and the sample, for deflecting the charged particle beam to cause the charged particle beam to be obliquely incident on the sample at an optional slant angle from a beam axis of the charged particle beam; a charged particle detector for detecting a secondary charged particle and/or a reflected charged particle which are generated from the sample irradiated with the charged particle beam; and a control part for controlling the slant angle.

According to the present invention, a slant observing deflecting device provided between the objective lens and the sample slants deflects charged particle beams immediately before the charged particle beams are incident on the sample, so that it is possible to acquire a slant image of the surface of the sample while preventing a deterioration of an electron-optics property due to the bending of the trajectory of the beams.

The control part may preferably include an irradiation position shift correcting part for correcting an irradiation position shift caused by the charged particle beam which is obliquely incident on the sample.

By the irradiation position shift correcting part, it is possible to easily correct the observation position of the slant image, so that it is possible to rapidly observe the slant.

It is preferable that the irradiation position shift correcting part has: an irradiation position shift quantity calculating part for calculating a magnitude and a direction of the irradiation position shift on the basis of the slant angle; and a scanning deflection control part for controlling the scanning deflecting device on the basis of the calculated result of the irradiation position shift quantity calculating part to shift the trajectory of the charged particle beam by a distance according to the magnitude of the irradiation position shift in the opposite direction to the direction of the irradiation position shift.

According to the second aspect of the invention, there is provided a charged particle beam system comprising:

a charged particle beam emitting device for generating a charged particle beam and for irradiating a sample to be inspected with the charged particle beam; a condenser lens for condensing the charged particle beam; an objective lens for focusing the charged particle beam on the surface of the sample; a scanning/slant observing deflecting device, arranged between the objective lens and the sample, for deflecting and scanning the charged particle beam and for causing the charged particle beam to be obliquely incident on the sample at an optional slant angle from a beam axis of the charged particle beam; a charged particle detector for detecting a secondary charged particle and/or a reflected charged particle which are generated from the sample irradiated with the charged particle beam; and a control part for controlling the slant angle.

According to the charged particle beam system, it is possible to simultaneously control the scanning deflection and slant observing deflection of electron beams since it has the scanning/slant observing deflecting device.

The charged particle beam system of the second aspect of the invention may advantageously further comprises: an irradiation position shift quantity calculating part for calculating a magnitude and a direction of an irradiation position shift, which occurs when the charged particle beam is obliquely incident on the sample, on the basis of the slant angle; and an irradiation position shift correcting part for controlling the scanning/slant observing deflecting device to correct the irradiation position shift on the basis of the calculated result of the irradiation position shift quantity calculating part.

The charged particle beam system of the second aspect of the invention may preferably further comprise a correction deflecting device, arranged between the condenser lens and the objective lens, for shifting the trajectory of the charged particle beam by a distance according to the magnitude of the position shift in the opposite direction to the direction of the position shift on the basis of the calculated results of the irradiation position shift quantity calculating part to correct the irradiation position shift, the correction deflecting device constituting an irradiation position shift correcting part.

The above mentioned charged particle beam system may further comprise a stage for supporting the sample, the stage being movable on a plane substantially perpendicular to the beam axis of the charged particle beams, and the irradiation position shift correcting part may include a stage control part for moving the stage by a distance according to the magnitude of the irradiation position shift in the direction of the irradiation position shift calculated by the irradiation position shift quantity calculating part, in place of the control of the scanning deflecting device or the scanning/slant observing deflecting device.

The charged particle beam system may further comprise an image processing part for converting the secondary charged particle and/or the reflected charged particle into image data, and a display for displaying the image data as a charged particle beam image, the secondary charged particle and/or the reflected charged particle being detected by the charged particle detector, and the irradiation position shift correcting part has an irradiation position shift quantity calculating part for calculating a magnitude and a direction of the irradiation position shift on the basis of the slant angle, and an image correcting part for controlling the image processing part so that the charged particle beam image is displayed at a desired position on the display on the basis of the calculated results, in place of the control of the scanning deflecting device, the scanning/slant observing deflecting device or the stage.

In addition, in place of the above mentioned control of the scanning deflecting device, the scanning/slant observing deflecting device, the stage or the image processing part, the irradiation position shift correcting part may further have an objective lens correction control part for controlling the objective lens on the basis of the calculated result of the irradiation position shift quantity calculating part to move the objective lens so that the trajectory of the charged particle beam shifted by the scanning deflecting control part passes through the center of the objective lens.

It is preferable that the objective lens correction control part electromagnetically moves the objective lens by shifting an electromagnetic field which is generated by the objective lens. Alternatively, the charged particle beam system may further comprise a movable lens supporting body for supporting the objective lens, and the objective lens correction control part may mechanically move the objective lens by moving the lens supporting body.

The control part of the charged particle beam system may preferably control the slant observing deflecting device or the scanning/slant observing deflecting device so that an ununiform electric field is generated at a position, at which the charged particle beam is emitted from the slant observing deflecting device or the scanning/slant observing deflecting device, or in a region in the vicinity of the point. Thus, the slant observing deflecting device or the scanning/slant observing deflecting device deflects the charged particle beams immediately before the charged particle beams are incident on the sample, to deflect the trajectory of the charged particle beams at the slant angle, so that it is possible to rapidly acquire the slant image of the surface of the sample while preventing the deterioration of the electron-optics property. Thus, it is possible to inspect the shape of the surface of the sample in-line. The ununiform electric or magnetic field can be formed by applying a DC voltage component to an electrode or coil, which is positioned in a direction for slanting the charged particle beams, of the electrodes or coils of the slant observing deflecting device or the scanning/slant observing deflecting device, and by applying no DC voltage component to the electrode or coil, which is positioned at the opposite direction, when the slant observing deflecting device or the scanning/slant observing deflecting device has the electrode or coil in the opposite direction to the direction in which the slant is intended.

The slant observing deflecting device or the scanning/slant observing deflecting device is preferably an electrostatic deflecting device. Thus, it can be more inexpensively prepared than a stage slant mechanism, so that it is possible to rapidly and easily carry out a slant observation with excellent linearity by retrofitting the existing systems.

The electrostatic deflecting device may advantageously include an insulator which is provided between the objective lens and the sample and on which a metal film is deposited, and the metal film constitutes an electrode of the electrostatic deflecting device.

Furthermore, the charged particle beam system may preferably further comprise a shielding electrode, incorporated in the electrostatic deflecting device, for shielding the objective lens from the electric field which is generated by the electrostatic deflecting device.

By the shielding electrode, an electric field shielding is formed between the bottom face of the objective lens and a region immediately before the charged particle beams are incident on the surface of the sample. Thus, it is possible to prevent a deterioration of an electron-optics property, such as lens aberration, of the charged particle beams.

According to the third aspect of the invention, there is provided a pattern slant observing method using a charged particle beam system which comprises a charged beam source, a charged particle beam optical system, a stage for supporting a sample on which a pattern is formed, and a charged particle detector, the electron-optical system including a scanning deflecting device and an objective lens, the pattern slant observing method comprising: an irradiation step of emitting a charged particle beam from the electron gun and of irradiating the sample with the charged particle beam; a scanning step of deflecting the charged particle beam by the scanning deflecting device to scan the charged particle beam on the sample; a focusing step of focusing the charged particle beam on the surface of the sample by the objective lens; a slant incident step of forming an ununiform electric field or an ununiform magnetic field at a position at which the charged particle beam is emitted from the electron-optical system or in a region in the vicinity of the position, of deflecting the charged particle beam by the electric or magnetic field so that the focused charged particle beam has an optional slant angle from a beam axis of the charged particle beam and of causing the charged particle beam to be obliquely incident on the sample; a detection step of detecting a secondary charged particle and/or a reflected charged particle which are generated from the sample by irradiation with the charged particle beam; and an image data acquiring step of acquiring image data, which are to be a slant image of the pattern, on the basis of the secondary charged particle and/or the reflected charged particle.

By the slant incident step, the charged particle beams are deflected by the ununiform electric or magnetic field, so that the charged particle beams are deflected intermediately before being incident on the sample, to be obliquely incident on the sample at the slant angle. Thus, it is possible to acquire the slant image of the pattern, which is formed on the surface of the sample, while preventing a deterioration of an electron-optics property.

The pattern slant observing method may advantageously further comprise an electromagnetic shielding step of preventing the electric or magnetic field from entering the trajectory of the charged particle beam on the side of the electron gun from a region in which the charged particle beam is deflected at the slant angle from the beam axis.

The pattern slant observing method may also advantageously further comprise an irradiation position shift quantity calculating step of calculating a magnitude and a direction of an irradiation position shift, which occurs when the charged particle beam is obliquely incident on the sample, on the basis of the slant angle, and the scanning step may include a step of shifting the trajectory of the charged particle beam by a distance according to the magnitude of the irradiation position shift in the opposite direction to the direction of the irradiation position shift on the basis of the calculated results at the irradiation position shift quantity calculating step. By the step of shifting the beam trajectory, the irradiation position shift of the charged particle beams is corrected, so that it is possible to rapidly observe the slant.

The pattern slant observing method may preferably further comprise a step of moving the objective lens on a plane substantially perpendicular to the beam axis of the charged particle beam in accordance with the shift of the trajectory of the charged particle beam so that the shifted charged particle beam passes through the center of the objective lens.

When the stage of the charged particle beam system is movable on a plane which is substantially perpendicular to the beam axis of the charged particle beams, the pattern slant observing method preferably further comprises a step of moving the stage in the direction of the irradiation position shift by a distance according to the irradiation position shift quantity on the basis of the calculated results at the irradiation position shift quantity calculating step, in place of the control of the scanning deflecting device or the scanning/slant observing deflecting device.

In addition, when the charged particle beam system further comprises a display for displaying the image data as a charged particle beam image, the pattern slant observing method may further comprise; an irradiation position shift quantity calculating step of calculating a magnitude and a direction of an irradiation position shift, which occurs when the charged particle beam is obliquely incident on the sample, on the basis of the slant angle; and an image correcting step of correcting the image data so that the charged particle beam image is displayed at a desired position on the display on the basis of the calculated results instead of the control of the scanning deflecting device, the scanning/slant observing deflecting device or the stage.

The scanning step of the pattern slant observing method may preferably be carried out simultaneously with the slant incident step at a position, at which the charged particle beam is emitted from the electron-optical system, or in a region in the vicinity of the position.

Furthermore, the pattern slant observing method may further comprise a correction deflecting step of shifting the trajectory of the charged particle beam by a distance according to the magnitude of the irradiation position shift in the opposite direction to the direction of the irradiation position shift, at the point at which the charged particle beam is emitted from the electron-optical system, or in a region in the vicinity of the point, or in a region which is more closer to the electron gun than the objective lens in the electron-optical system, on the basis of the calculated results at the irradiation position shift quantity calculating step instead of the control of the scanning deflecting device, the scanning/slant observing deflecting device, the stage or the image processing part.

DESCRIPTION OF THE PREFERRED EMBODIMENTS

Referring now to the accompanying drawings, some preferred embodiment of the present invention will be described below. Furthermore, the same reference numbers are given to the same portions in the respective figures, and the descriptions thereof are omitted.

(1) First Preferred Embodiment

Figure 1:
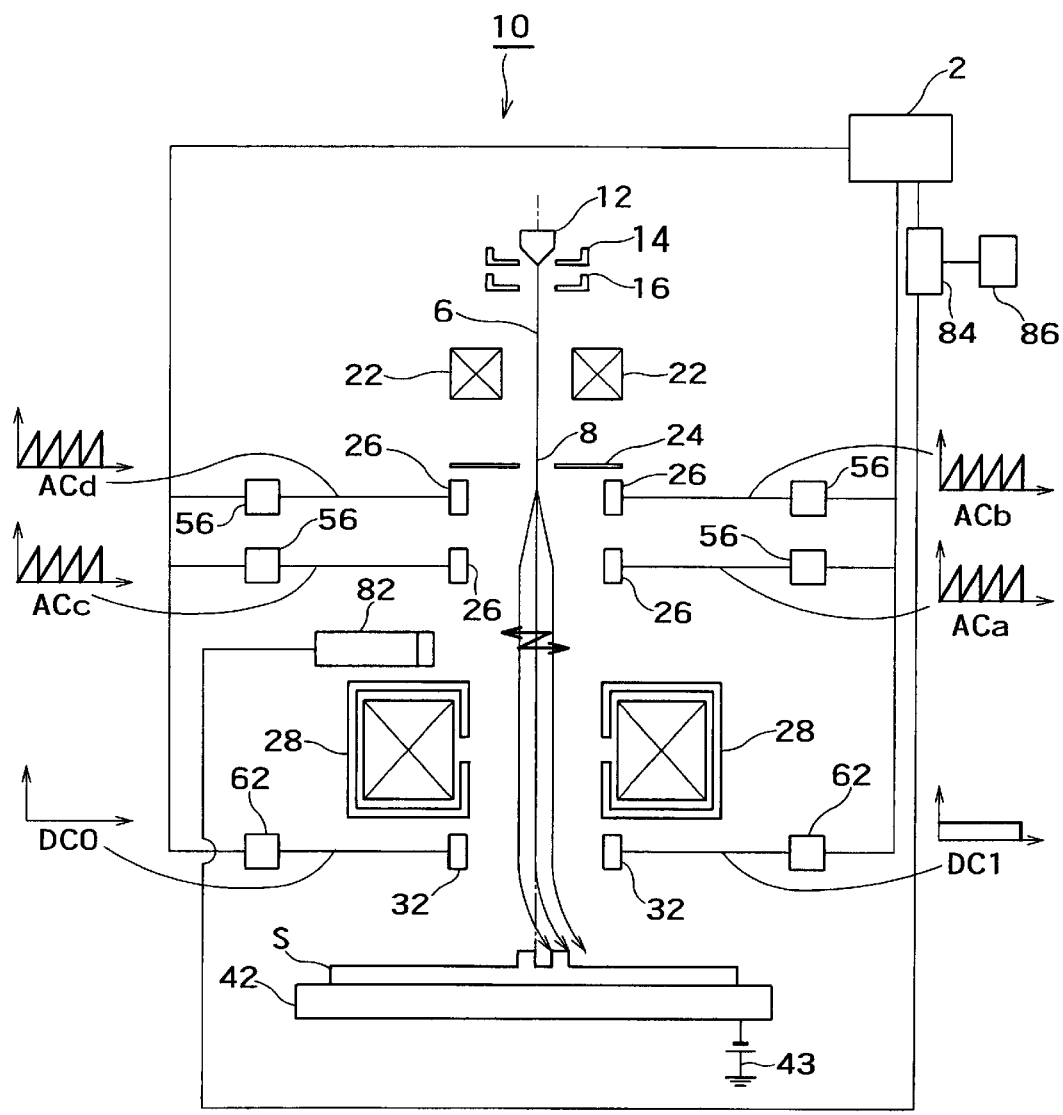
FIG. 1 is a schematic diagram showing the first preferred embodiment of a charged particle beam system according to the present invention.

FIG. 1 is a schematic diagram showing the first preferred embodiment of a charged particle beam system according to the present invention. In this figure, the feature of a charged particle beam system 10 in this preferred embodiment is that a slant observing deflecting device 32 is provided between an objective lens 28 and a sample S.

First, the schematic construction of this preferred embodiment will be described. The charged particle beam system 10 shown in FIG. 10 comprises an electron gun part, an electron-optical system, a stage, a secondary electron image acquiring part, and a control part.

The stage 42 has a mechanism capable of moving in optional directions on a horizontal plane. The sample S is supported on the top face of the stage 42. The stage 42 is connected to a power supply 43 to apply an optional voltage on the sample S. Thus, a retarding field is formed above the sample S.

The electron gun part includes an electron gun 12, an extraction electrode 14, and an acceleration electrode 16. The electron gun 12 emits electrons when a voltage is applied thereto. The extraction electrode 14 extracts the emission electrodes when a voltage is applied thereto. The acceleration electrode 16 accelerates the extracted emission electrodes to cause the electrons to be incident on the electron-optical system as electron beams 6.

The electron-optical system includes a condenser lens 22, a scanning deflecting device 26, the objective lens 28, and the slant observing deflecting device 32 which is one of the feature in this preferred embodiment.

The condenser lens 22 condenses the electron beams 6, which have passed through the acceleration electrode 16, to cause the condensed electron beams 6 to pass through a diaphragm 24. The scanning deflecting device 26 receives a serrate signal ACa through ACd from a scanning deflection control part 56, which will be described later, to scan and deflect the electron beams 26 which have passed through the diaphragm 24. The objective lens 28 condenses the scanned primary electron beams 6 to form an image on the top of the sample S. Between the objective lens 28 and the sample S, the slant observing deflecting device 32 is provided. In this preferred embodiment, the slant observing deflecting device 32 is an electrostatic deflecting device 32. The detailed construction and calculation of the slant observing deflecting device 32 will be described later.

The secondary electron image acquiring part has a secondary electron detector 82, an image processing part 84 and monitor 86.

When the sample S is irradiated with the electron beams 6, secondary electrons and reflected electrons (which will be hereinafter referred to as secondary electrons and so forth) are generated. After the generated secondary electrons and so forth pass through the objective lens 28 while being accelerated by the retarding field formed between the sample S and the objective lens, the secondary electrons are drawn into the secondary electron detector 82. The secondary electrons and so forth detected by the secondary electron detector 82 are converted into electric signals by the image processing part 84 to be amplified to be supplied to the monitor 86. The monitor 86 displays a secondary electron image indicative of the state of the surface of the sample S.

The control part comprises a control computer 2, the scanning deflection control part 56, and a slant observing deflection control part 62. The control computer 2 controls the whole system. The scanning deflection control part 56 is connected to the scanning deflecting device 26, and sets the above described serrate signal ACa through ACd on the basis of command signals, which are supplied from the control computer 2, and supplies the set serrate signal ACa through ACd to the scanning deflecting device 26. The slant observing deflection control part 62 is connected to the slant observing deflecting device 32, and sets a slant observing DC voltage DC1 on the basis of control signals, which are supplied from the control computer 2 and applies the DC voltage to the slant observing deflecting device 32.

Figure 2A:
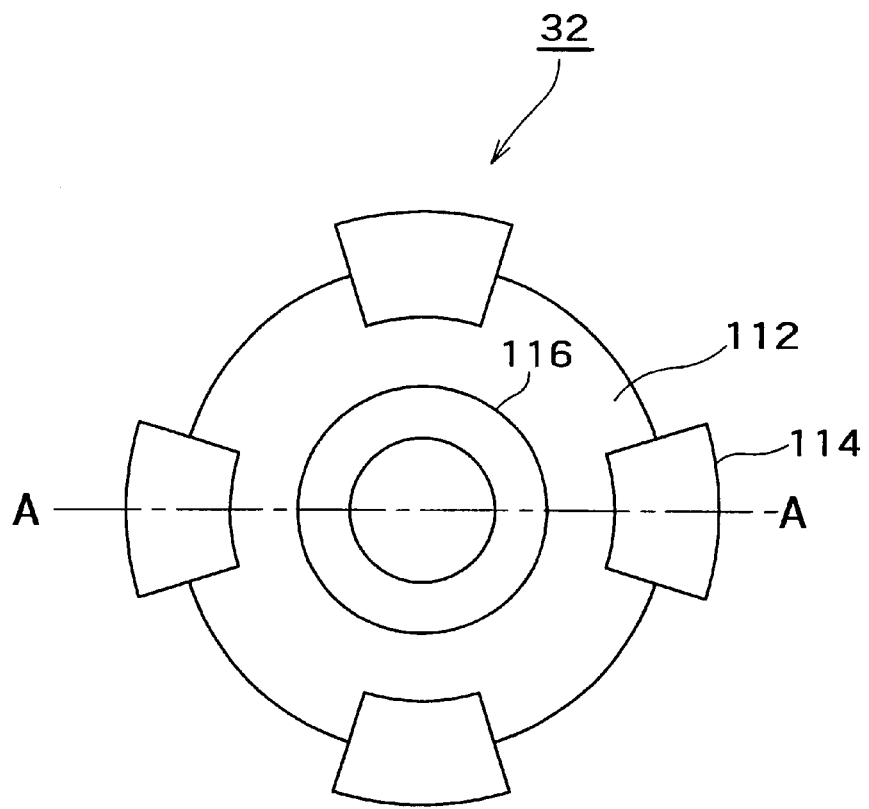
FIGS. 2A and 2B are bottom and sectional views schematically showing a slant observing deflecting device shown in FIG. 1.
Figure 2B:
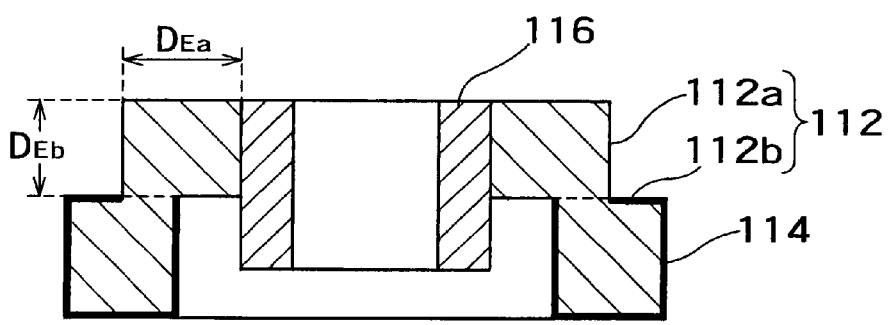

FIG. 2A is a bottom view schematically showing the slant observing deflecting device 32, and FIG. 2B is a sectional view taken along line A—A of FIG. 2A. In the charged particle beam system 10, the distance between the objective lens 28 and the sample S is generally very short, about a few mm. In this preferred embodiment, this distance is 2.5 mm. Therefore, the slant observing deflecting device 32 must be compact and simple.

As shown in FIGS. 2A and 2B, the slant observing deflecting device 32 comprises a body 112, a sleeve 116, and four electrodes 114. In this preferred embodiment, the slant observing deflecting device 32 is mounted so that the top faces of the body 112 and sleeve 116 contact the bottom face of the objective lens.

The body 112 includes a ring-shaped body portion 112a, and four protruding portions 112b which are formed on the peripheral edge portion of the bottom face of the body portion 112. In this preferred embodiment, the body portion 112a and the protruding portions 112b are integrally formed of an insulator. The protruding portions 112b are arranged along a concentric circle about the center of beam axes so as to protrude outwardly from the outer peripheral edge of the body portion 112a. The peripheral and bottom surfaces of the protruding portions 112b are plated with gold to construct the electrodes 114. Each of the electrodes 114 is connected to the slant observing deflection control part 62 by means of wires so that a voltage can be applied thereto.

Since the voltage applied to the electrodes 114 has a value of a few kV, there is the possibility that discharge may occur between the electrodes 114 and the bottom face of the objective lens 28. In this preferred embodiment, a sufficient edge face distance ($D_{Ea}+D_{Eb}$ in the figure) is ensured by adopting the above described structure using the insulator.

The sleeve 116 is mounted on the inner peripheral surface of the body 112. The sleeve 116 has a cylindrical shape which has a central axis common to the central axis of the body portion 112a. The bottom face of the sleeve 116 is formed so as to protrude from the bottom face of the body portion 112a toward the sample S. With such shape and arrangement, an electric field shielding is formed in a region extending from the bottom face of the objective lens 28 immediately before the electron beams 6 are incident on the surface of the sample. Thus, it is possible to prevent a deterioration of an electron-optics property such as lens aberration of the electron beams 6.

The deflection angle and deflected direction of the electron beams 6 are controlled by set values of the respective slant observing deflection control parts 62. That is, since the slant observing deflecting device 32 in this preferred embodiment is an electrostatic deflecting device, the deflection angle and deflected direction can be controlled by DC voltage components applied to the electrodes 114. If different DC voltages are applied to the two facing electrodes 114, respectively, an ununiform electric field is formed between the electrodes 114 and below the electrodes 114. This ununiform electric field changes the deflected direction of the electron beams 6 to only one direction. Thus, the electron beams 6 can be slanted.

Figure 3:
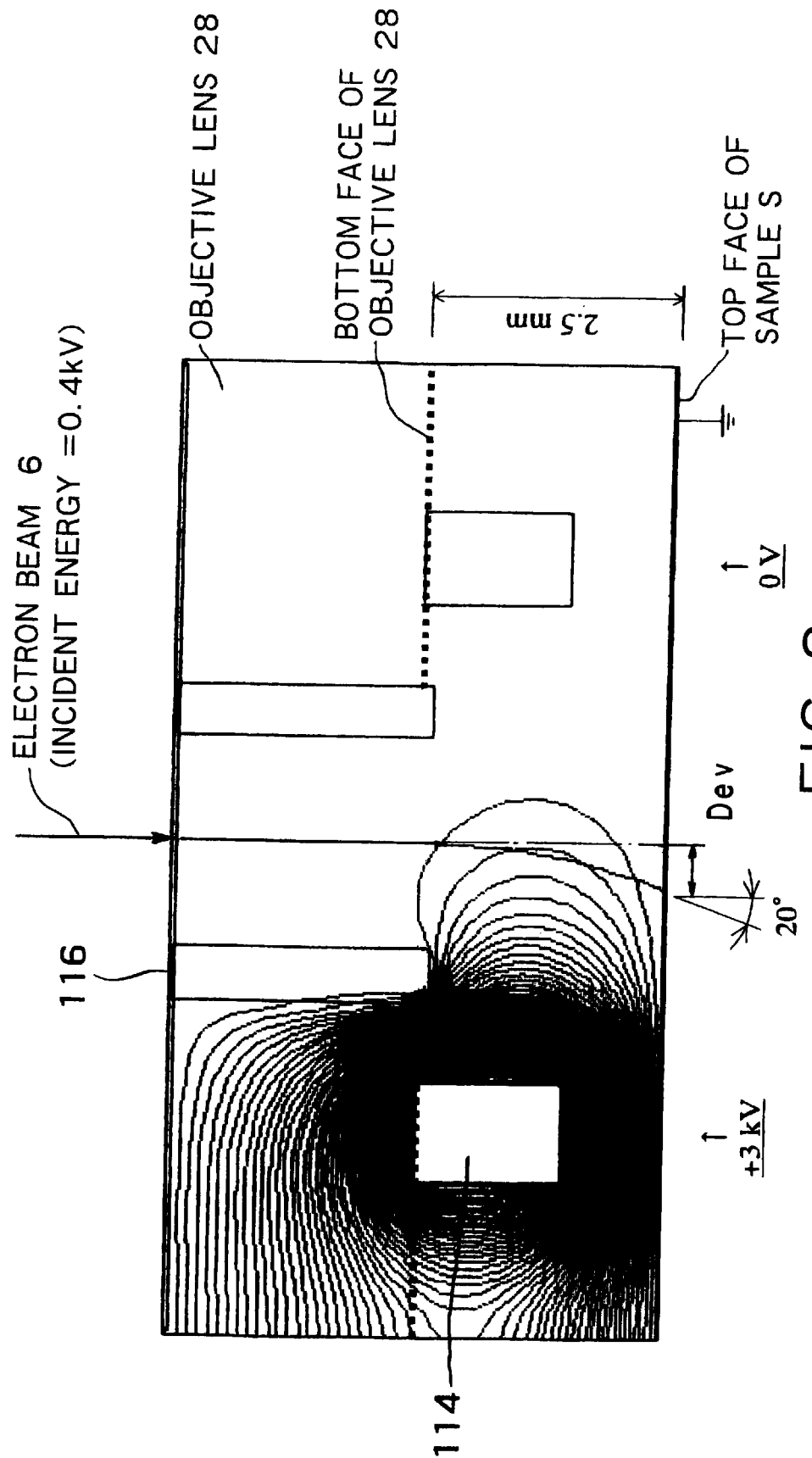
FIG. 3 is an illustration showing an example of equipotential lines for explaining the calculation of a slant observing electrostatic deflecting device shown in FIGS. 2A and 2B.

FIG. 3 shows an example of equipotential lines which are numerically calculated when 0 V and +3.0 kV are applied to the two facing electrodes 114a and 114b, respectively. The distance between the objective lens 28 and the sample S is 2.5 mm, the incident voltage on the sample S is 0.4 kV, and the sample voltage is 0 V. As can be seen from this figure, an electric field is formed about the electrode 114a to which the voltage of 3.0 kV is applied. Below the sleeve 116, the electric field projects toward the trajectories of the electron beams 6. By such an ununiform electric field, the trajectories of the electron beams 6 extending vertically downwards are bent to be attracted toward the electrode 114a to which the voltage has been applied. As a result, the electron beams 6 are incident on the sample S at a deflection angle of about 20° while focusing by the force applied by the objective lens 28. By the irradiation with such slanted electron beams 6, the secondary electron image displayed on the monitor 86 is an image wherein the sample S is slanted by 20°.

Figure 4:
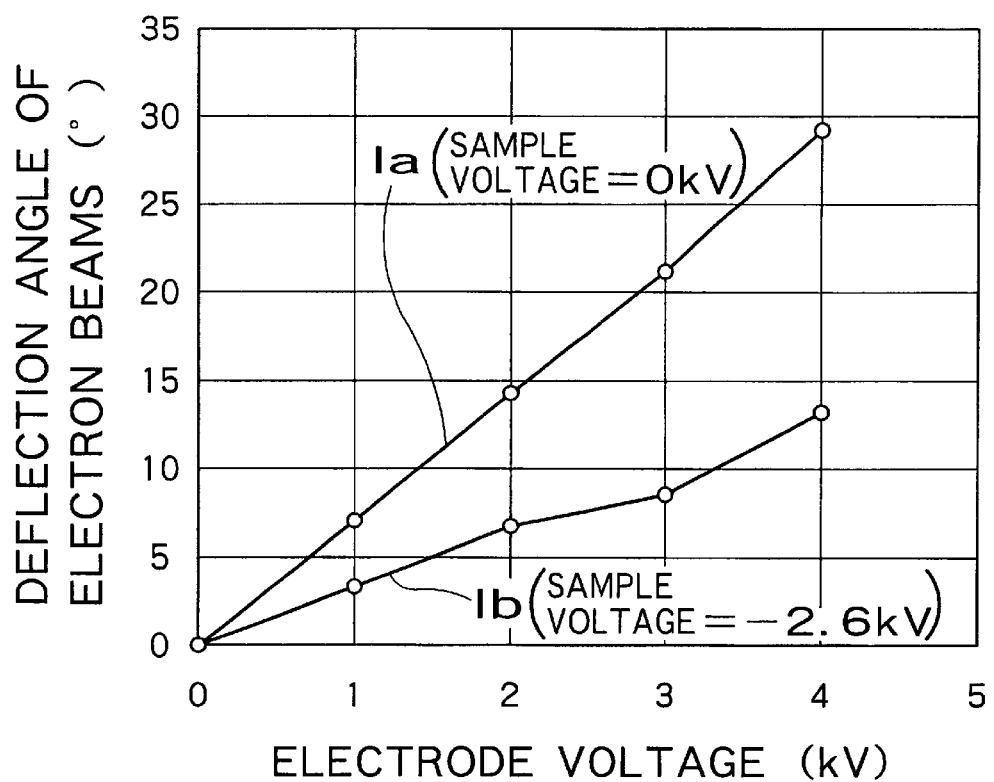
FIG. 4 is a graph showing the relationship between a voltage applied to the slant observing electrostatic deflecting device shown in FIGS. 2A and 2B, and a deflection angle of electron beams.

FIG. 4 shows the deflection angle of the electron beams 6 when the electrode voltage is changed from 0 V to 4 kV. In this figure, a line la drawn between marks ○ shows the deflection angle when the sample voltage =0V, and a line 1b drawn between marks Δ shows the deflection angle when the sample voltage=−2.6 kV (electron beam 6=+3.0 kV). It can be seen from this figure that the deflection angle of the electron beams 6 is linearly changed by the DC voltage applied to the electrode 114a. From this, it can be seen that the deflection angle can be obtained by calculation or experiment if the electrode voltage, the energy of the electron beams 6 and the sample voltage are known. It can also be seen from this figure that the slant can be observed regardless of the presence of the retarding field.

While the two facing electrodes 114a and 114b have been described in FIGS. 3 and 4 for simple explanation, the deflection angle can be changed in optional directions if different DC voltages are applied to the four electrodes 114a through 114d, respectively. Thus, it is possible to obtain an optional slant image. In order to obtain the three-dimensional information on the sample S, the slant observing deflecting device 32 must have a very large deflection angle (1° or more) as compared with the deflection angle (about 0.2°) of the scanning deflecting device 26. Although FIG. 1 shows an example where a voltage of 0 V is applied to the left electrode 114, the trajectories of the electron beams 6 can be bent if a potential difference occurs between electrodes.

Figure 5:
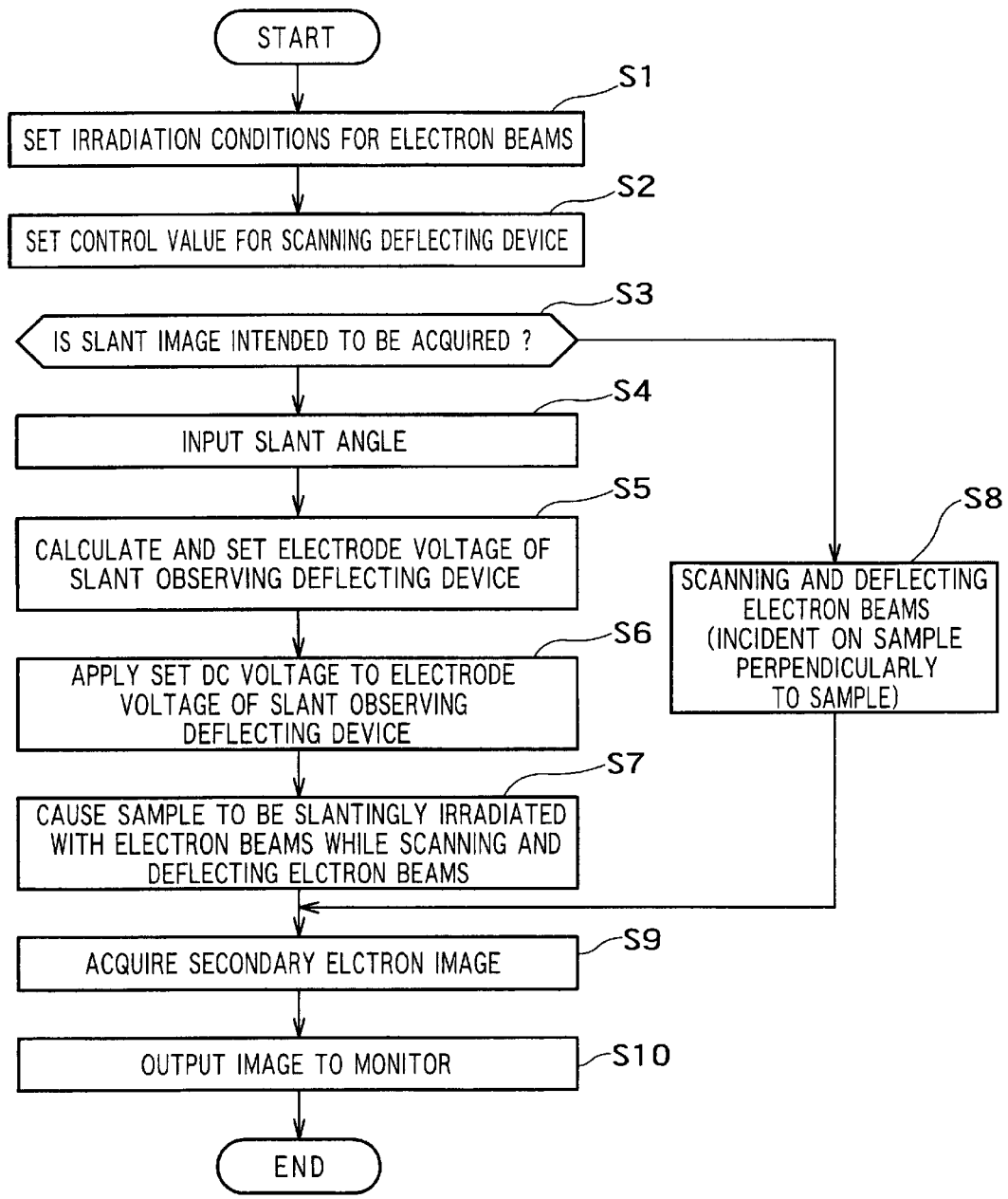
FIG. 5 is a flow chart for explaining the procedure for carrying out a pattern slant observing method according to the present invention.

FIG. 5 is a flow chart showing the procedure for acquiring a secondary electron image using the charged particle beam system 10 shown in FIG. 1. In this figure, steps S1 through S7, S9 and S10 show the procedure for carrying out a pattern slant observing method.

First, irradiation conditions, such as acceleration voltages and beam currents, for the electron beams 6 are set (step S1). Then, the control values of the scanning deflecting device 26 are set (step S2). The setting of these conditions and values is carried out by inputting setting values to the control computer 2.

When a slant image is not intended to be acquired (step S3), the charged particle beam system 10 scans and deflects electron beams 6 to cause the electron beams 6 to be incident on the sample S in a direction perpendicular thereto in the same manner as the conventional manner (step S8). Thus, a secondary electron image is acquired (step S9), and a top-down image is outputted to the monitor 86 (step S10).

When an slant image is intended to be acquired (step S3), a slant angle at which the sample S is to be observed (which will be hereinafter referred to as a "target slant angle") is inputted from the control computer 2 (step S4). Thus, the control computer 2 calculates a DC voltage, which slants the electron beams 6 at the target slant angle, on the basis of the irradiation conditions, sample applied voltage and so forth by means of an calculation part (not shown), and then, supplies a control signal to the slant observing deflection control part 62 (step S5). The slant observing deflection control part 62 sets a DC voltage value on the basis of the control signal, and the set DC voltage is applied to the corresponding electrostatic electrodes 114 of the slant observing deflecting device 32 (step S6). As a result, as described above, the electron beams 6 are deflected by the ununiform electric field, which is formed by the slant observing deflecting device 32, while being scanned and deflected by the electric field of the objective lens 28, so that the electron beams 6 are obliquely incident on the sample S (step S7). Thereafter, secondary electrons and so forth, which are generated from the sample S by the incidence of the electron beams 6, are incorporated into the secondary electron detector 82 to acquire a secondary electron image (step S9) to display a slant image on the monitor 86 (step S10).

Furthermore, in the slant observing deflecting device 32 of the charged particle beam system 10 shown in FIG. 1, the number of the electrodes 114 may be changed in accordance with uses. If the direction to be slanted is one direction, the number of the electrodes 114 may be at least one, and if it is required to obtain slant images in optional directions, the number of the electrodes 114 must be four or more.

While the electrostatic deflecting device and electrodes having excellent rapid deflection and linearity have been used in the above described first preferred embodiment, the combination of a magnetic deflecting device and a coil may be used for bending the trajectories of the electron beams 6 to observe the slant.

(2) Second Preferred Embodiment

Referring to the accompanying drawing, the second preferred embodiment of a charged particle beam system according to the present invention will be described below.

Figure 6:
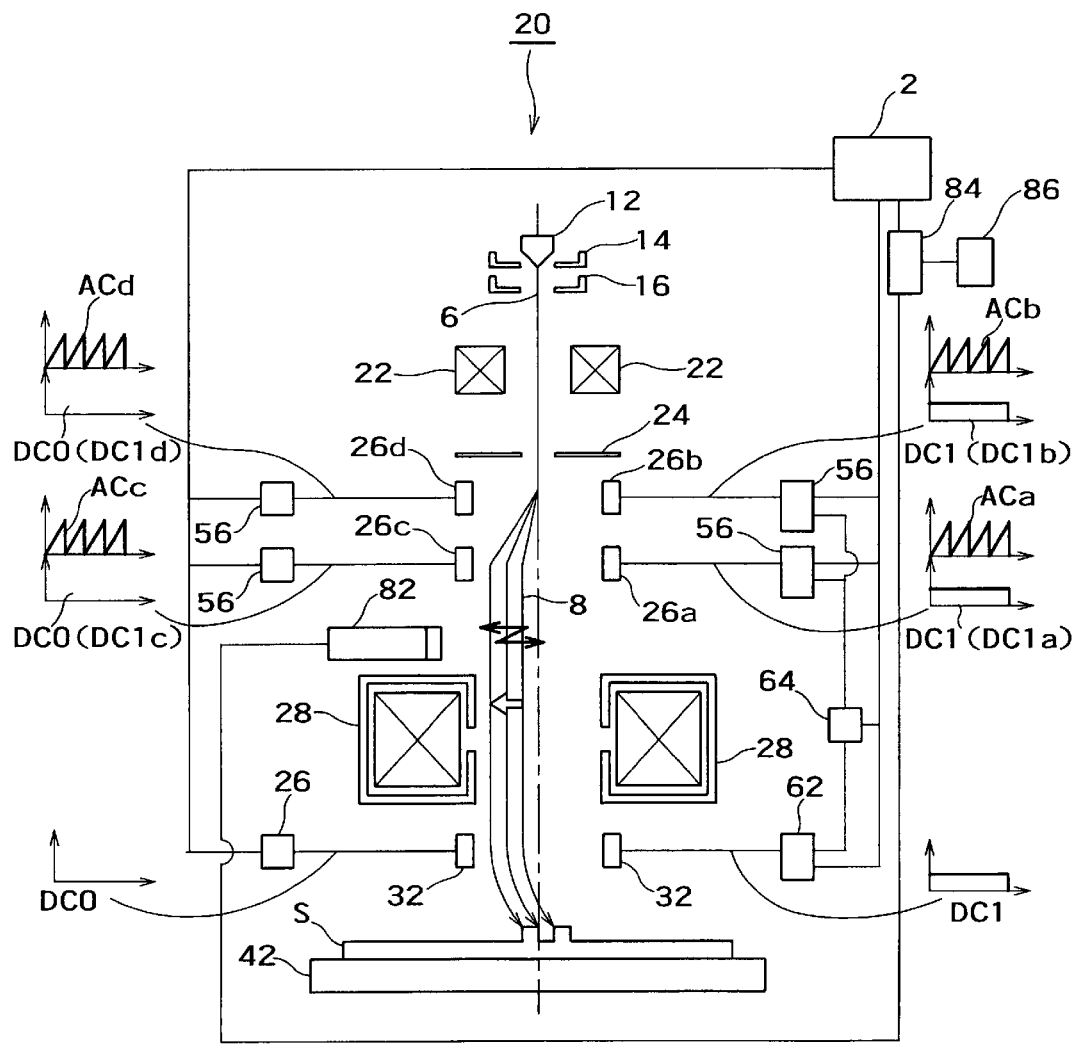
FIG. 6 is a schematic diagram showing the second preferred embodiment of a charged particle beam system according to the present invention.

FIG. 6 is a schematic diagram showing the construction of a charged particle beam system 20 in this preferred embodiment. As shown in this figure, the charged particle beam system 20 in this preferred embodiment is characterized in that the system 20 further comprises a correction deflection calculating part 64 connected to the slant observing deflection control part 62 and the scanning deflection control part 56, in addition to the construction shown in FIG. 1. Other constructions of the system 10 are substantially the same as those of the charged particle beam system 10 of FIG. 1. Furthermore, the correction deflection calculating part 64 is connected to the control computer 2 and to all of the slant observing deflection control parts 62 and all of the scanning deflection control parts 56 although the details thereof are not shown in the figure.

In the charged particle beam system 10 shown in FIG. 1, although it is possible to obtain a slant image since the electron beams 6 are deflected by the slant observing deflecting device 32, a shift Dev of the irradiation position of the electron beams 6 with which the sample S is irradiated occurs as shown in FIG. 3. In the charged particle beam system 20 shown in FIG. 6, the correction deflection calculating part 64 calculates the quantity of such a shift of the irradiation position (which will be hereinafter referred to as an "irradiation position shift") and controls the scanning deflecting device 26 via the scanning deflection control part 56 to correct the irradiation position shift. In this preferred embodiment, the control computer 2, the correction deflection control part 64 and the scanning deflecting device 26 constitute an irradiation position shift correcting part.

The procedure for correcting the irradiation position by the charged particle beam system 20 shown in FIG. 6 will be described below.

First, the control computer 2 supplies a slant observing control signal to the slant observing deflection control part 62 and supplies data, such as a deflection angle and energy of electron beams 6, to the correction deflection calculating part 64. As described above in the first preferred embodiment, the slant observing deflection control part 62 receives the control signal from the control computer 2, sets a DC component DC1 and supplies an input signal, which is to be inputted to the slant observing deflecting device 32, to the correction deflection calculating part 64. The correction deflection calculating part 64 calculates an irradiation position shift quantity of the electron beams 6 using data on the deflection angle and energy of the electron beams 6, and the input signal which is to be inputted to the slant observing deflecting device 32, as parameters. On the basis of the calculated results, the correction deflection calculating part 64 supplies a control signal for irradiation position shift correction to the scanning deflection control part 56. Then, the scanning deflection control part 56 sets DC components DC1a through DC1d capable of correcting the irradiation position shift of the electron beams 6. The DC voltage component DC1 is applied to the electrode 114 of the slant observing deflecting device 32, and the DC components DC1a through DC1d are simultaneously applied to the scanning deflecting devices 26a through 26d. In the embodiment shown in FIG. 6, the DC components DC1c and DC1d have a value of 0. As a result, the trajectories 8 of the electron beams 6 are shifted in a direction, in which the irradiation position shift is corrected, so that it is possible to avoid the shift of the observation region by the slant deflection.

(3) Third Preferred Embodiment

Referring to the accompanying drawing, the third preferred embodiment of a charged particle beam system according to the present invention will be described below.

Figure 7:
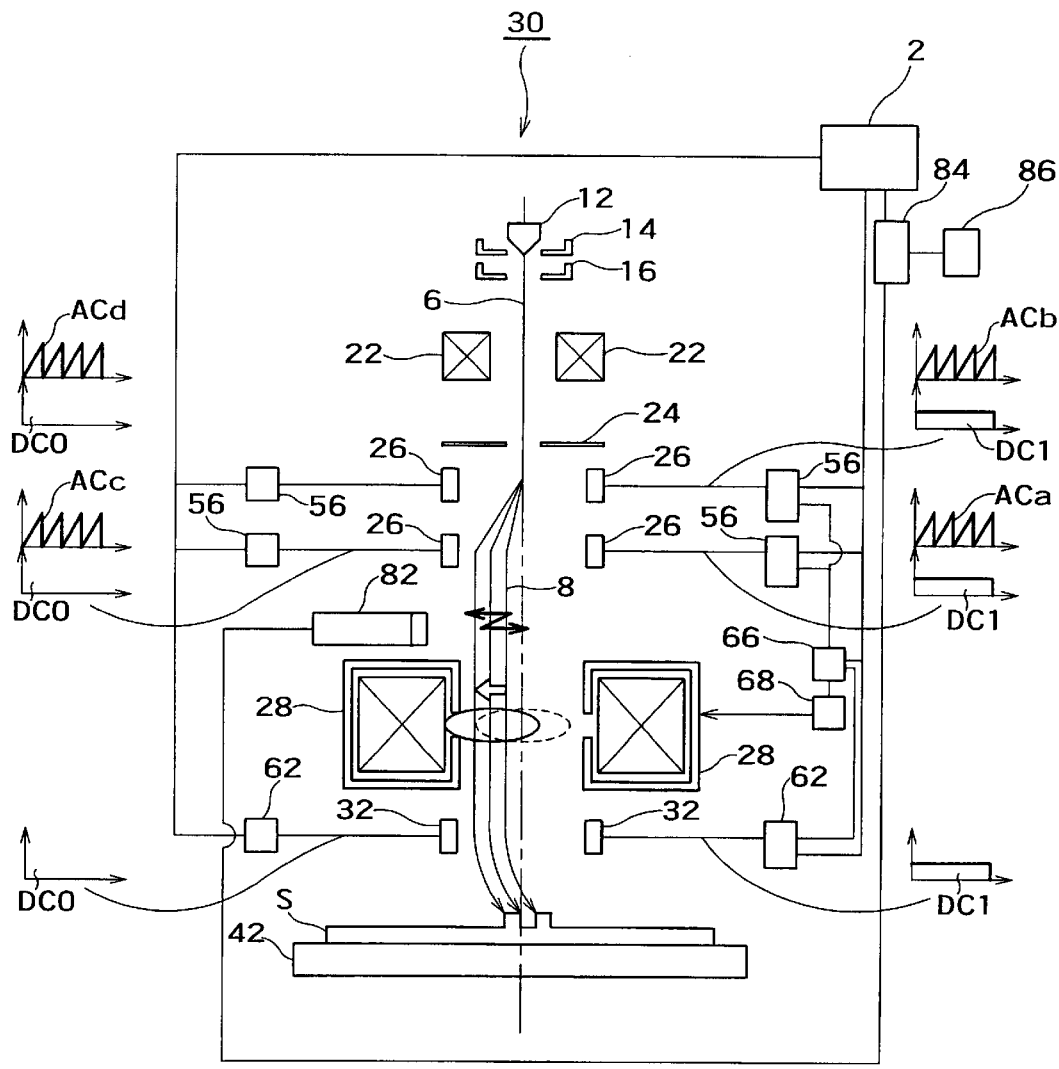
FIG. 7 is a schematic diagram showing the third preferred embodiment of a charged particle beam system according to the present invention.

FIG. 7 is a schematic diagram showing the construction of a charged particle beam system 30 in this preferred embodiment. As shown in this figure, the charged particle beam system 30 in this preferred embodiment is characterized in that the system 30 further comprises a correction deflection calculating part 66 and an objective lens correction control part 68, in addition to the construction shown in FIG. 1. The correction deflection calculating part 66 is connected to the control computer 2 and to all of the scanning deflection control parts 56, the objective lens correction control part 68 and the slant observing deflection control part 62. Other constructions of the system 30 are substantially the same as those of the charged particle beam system 10 of FIG. 1.

In the charged particle beam system 20 shown in FIG. 1, there is no problem when the magnitude of the irradiation position shift is small, e.g., a few µm. However, the magnitude increases to, e.g., tens µm, the trajectories 8 of the electron beams 6 are greatly spaced from the center of the objective lens 28, so that electron-optical characteristics may deteriorate. In this preferred embodiment, the trajectories 8 of the electron beams 6 are shifted by the scanning deflecting device 26, and the center of the objective lens 28 is shifted to the position after the trajectories 8 of the electron beams 6 are shifted, so that a deterioration of an electron-optics property is prevented.

The procedure for correcting an irradiation position shift in the charged particle beam system 30 shown in FIG. 7 will be described below.

First, the control computer 2 supplies data on a deflection angle and energy of the electron beams 6 to the slant observing deflection control part 62 and the correction deflection calculating part 66. The slant observing deflection control part 62 sets a DC voltage component DC1 as an input signal which is to be inputted to the electrode 114 of the slant observing deflecting device 32 and supplies the input signal to the correction deflection calculating part 66. The correction deflection calculating part 66 calculates an irradiation position shift quantity of the electron beams 6 using data on the deflection angle and energy of the electron beams 6, and the input signal which is to be inputted to the slant observing deflecting device 32, as parameters. On the basis of the calculated results, the correction deflection calculating part 66 supplies a control signal for irradiation position shift correction to the scanning deflection control part 56 and the objective lens correction control part 68. Then, the DC voltage component DC1 is applied to one of the electrodes 114 of the slant observing deflecting device 32 (the right electrode in the embodiment of FIG. 7), and the DC voltage components DC1 is applied to a corresponding electrode of each of the scanning deflecting devices 26 (the right electrode in the embodiment of FIG. 7). Simultaneously, the objective lens correction control part 68 controls the objective lens 28 so that the center of the objective lens 28 is shifted to the corrected position of the electron beams 6. Thus, the central portion of the objective lens 28 is coincident with the trajectories 8 of the electron beams 6.

Thus, according to this preferred embodiment, the irradiation position shift is corrected by both of the scanning deflecting device 26 and the objective lens 28, so that it is possible to observe a slant image while maintaining the electron-optics property even if the slant angle of the electron beams 6 is large to greatly change the observation position.

(4) Fourth Preferred Embodiment

Referring to the accompanying drawing, the fourth preferred embodiment of a charged particle beam system according to the present invention will be described below.

Figure 8:
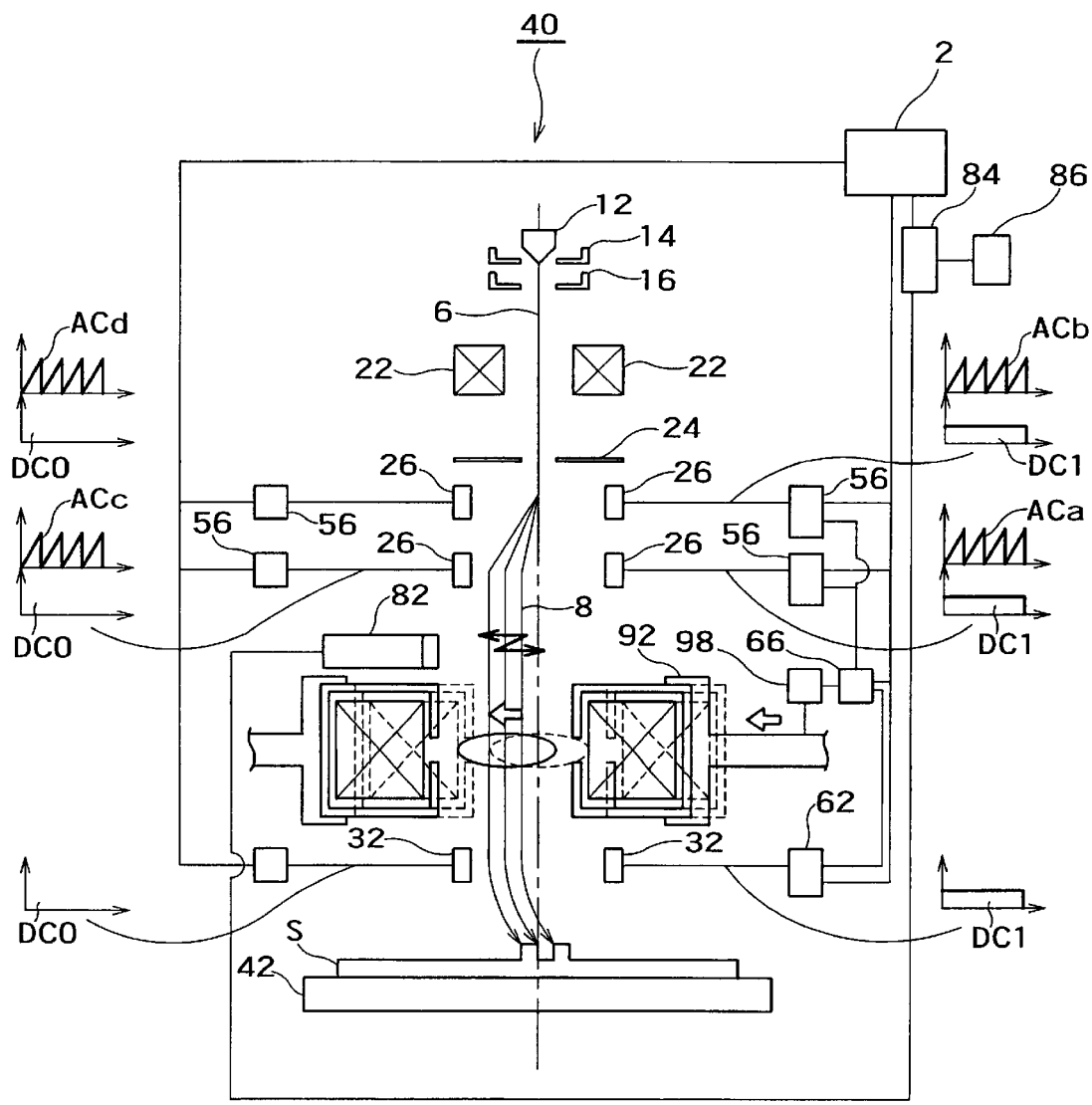
FIG. 8 is a schematic diagram showing the fourth preferred embodiment of a charged particle beam system according to the present invention.

FIG. 8 is a schematic diagram showing the construction of a charged particle beam system 40 in this preferred embodiment. As can be seen from the comparison with the charged particle beam system 30 shown in FIG. 7, the charged particle beam system 40 in this preferred embodiment is characterized in that the system 40 further comprises an objective lens holding part 92, and an objective lens holding control part 98 substituted for the objective lens correction control part 68. Other constructions of the charged particle beam system 40 are substantially the same as those of the charged particle beam system 30 of FIG. 7.

The objective lens holding part 92 holds the objective lens 28, and receives a control signal from the objective lens holding control part 98 to move the objective lens 28 on a plane perpendicular to the beam axis 8 during a slant observation. That is, the correction deflection calculating part 66 calculates an irradiation position shift quantity to supply a control signal for irradiation position shift correction to the scanning deflecting control part 56 and the objective lens holding control part 98. Then, a DC voltage component DC1 is applied to one of the electrodes 114 of the slant observing deflecting device 32 (the right electrode in the embodiment of FIG. 8), and the DC voltage components DC1 is applied to a corresponding electrode of each of the scanning deflecting devices 26 (the right electrode in the embodiment of FIG. 8) by the scanning deflecting part 56. Simultaneously, the objective lens holding control part 98 moves the objective lens 28 by a distance according to the magnitude of the irradiation position shift quantity in a direction, in which the irradiation position of the electron beams 6 is shifted, on the basis of a control signal from the correction deflection calculating part 66. Thus, the central portion of the objective lens 28 is coincident with the trajectories 8 of the electron beams 6.

Thus, also according to this preferred embodiment, the irradiation position shift is corrected by both of the scanning deflecting device 26 and the objective lens 28, so that it is possible to observe a slant image while maintaining an electron-optics property even if the observation position is greatly changed due to a large slant angle of the electron beams 6.

(5) Fifth Preferred Embodiment

Referring to the accompanying drawing, the fifth preferred embodiment of a charged particle beam system according to the present invention will be described below.

Figure 9:
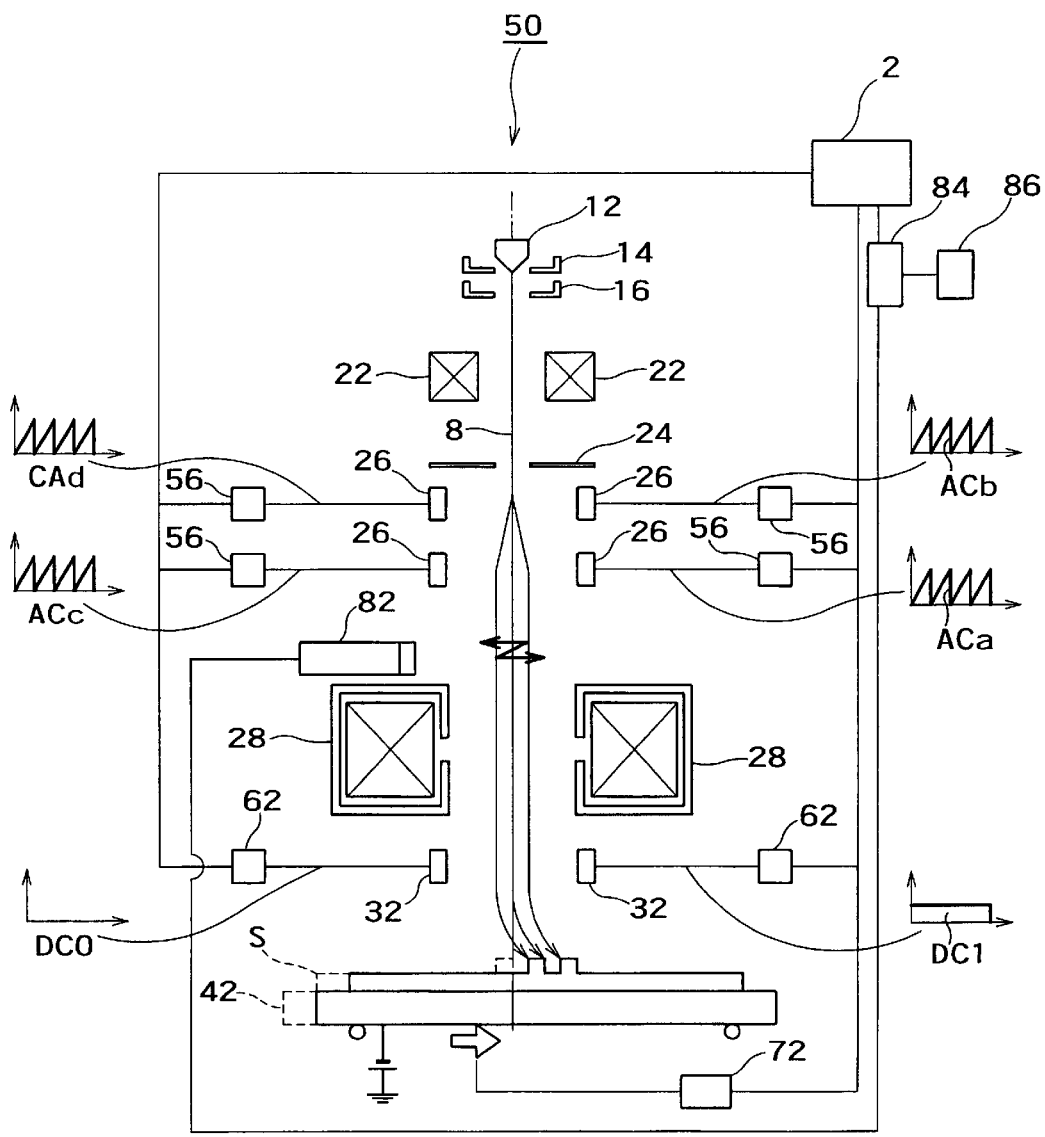
FIG. 9 is a schematic diagram showing the fifth preferred embodiment of a charged particle beam system according to the present invention.

FIG. 9 is a schematic diagram showing the construction of a charged particle beam system 50 in this preferred embodiment. As shown in this figure, the charged particle beam system 50 in this preferred embodiment is characterized in that the system 50 further comprises a stage control part 72 for controlling the stage 42, so that the irradiation position shift of the electron beams 6 is corrected by the movement of the stage. Other constructions of the charged particle beam system 50 are substantially the same as those of the charged particle beam system 10 of FIG. 1. In this preferred embodiment, the control computer 2 also constitutes an irradiation position shift quantity calculating part.

The procedure for correcting the irradiation position shift of the electron beams 6 by the charged particle beam system 50 shown in FIG. 9 will be described below.

First, the control computer 2 calculates an irradiation position shift quantity of the electron beams 6 using an input signal which is to be inputted to the slant observing deflecting device 62, and data on a deflection angle and energy of the electron beams 6, as parameters. On the basis of the calculated results, the control computer 2 supplies a control signal for irradiation position shift correction to the stage control part 72. This control signal includes information on a direction, in which the irradiation position is shifted, and on the distance between the original irradiation position, at which the sample is vertically irradiated with the electron beams 6, and a position at which the slant electron beams 6 reach the surface of the sample. The stage control part 72 feeds a movement command to the stage 42 on the basis of the control signal. Thus, the stage 42 moves in the calculated direction by the calculated distance. As shown in FIG. 8, the stage 42 can move the sample S from a position, at which observation is carried out before the electron beams 6 are slanted and deflected, so that the target position is displayed on the slant image on the monitor.

Thus, according to this preferred embodiment, the irradiation position shift is corrected by the movement of the stage 42, so that no additional operation is required for the electron-optical system mainly including the scanning deflecting device 28 and the objective lens 28. For that reason, it is possible to observe a slant image without fearing a deterioration of an electron-optics property.

(6) Sixth Preferred Embodiment

Figure 10:
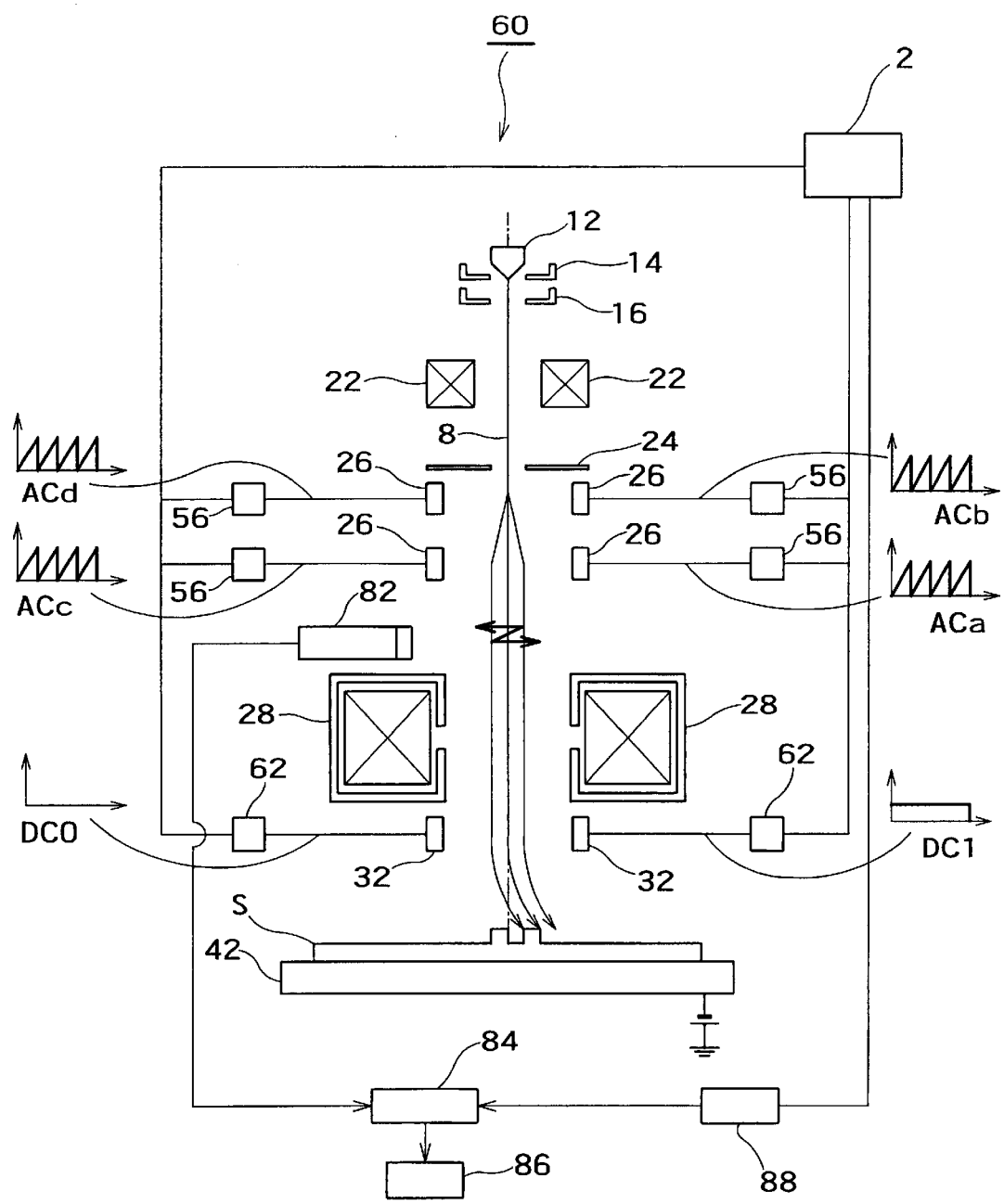
FIG. 10 is a schematic diagram showing the sixth preferred embodiment of a charged particle beam system according to the present invention.

FIG. 10 is a schematic diagram showing the sixth preferred embodiment of a charged particle beam system according to the present invention. The charged particle beam system 60 shown in this figure is characterized in that the system 60 further comprises an image processing control part 88 in addition to the construction of the charged particle beam system 10 shown in FIG. 1, so that the irradiation position shift of the electron beams 6 is corrected by the image processing. Other constructions of the charged particle beam system 60 are substantially the same as those of the charged particle beam system 10 of FIG. 1. Also in this preferred embodiment, the control computer 2 also constitutes an irradiation position shift quantity calculating part.

Figure 11A:
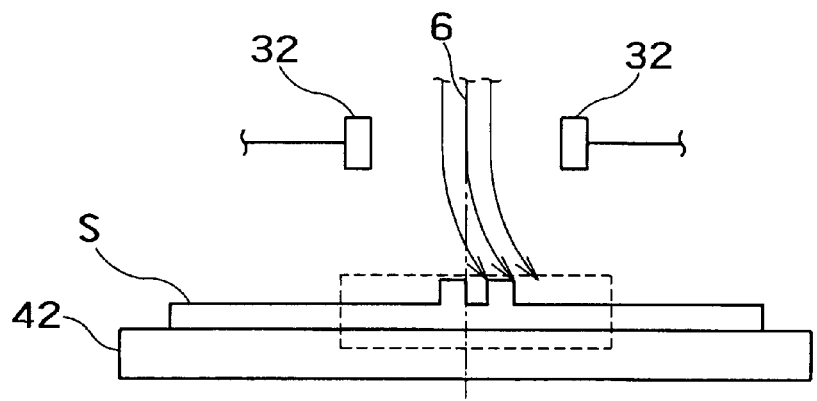
FIGS. 11A through 11C are illustrations for explaining a method for correcting the shift of the irradiation position electron beams with which a sample is irradiated.
Figure 11B:
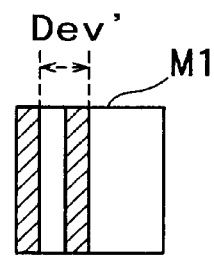
Figure 11C:
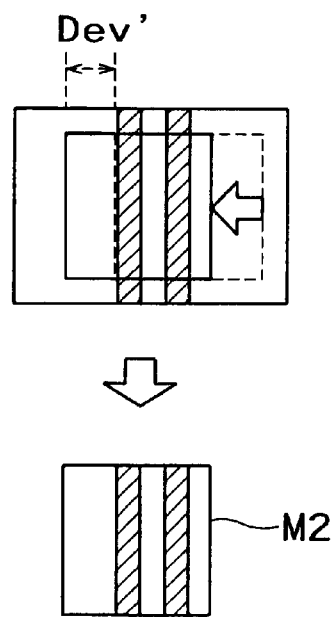

Referring to FIGS. 11A through 11C, the procedure for correcting the irradiation position shift by the charged particle beam system 60 shown in FIG. 10 will be described below.

FIG. 11A shows a state that electron beams 6 are obliquely incident on the surface of a sample by the procedure shown in FIG. 5. In the example of FIG. 11A a pattern having two protrusions substantially at the center on the top face of a sample S is formed. If the electron beams 6 are incident on the surface of the sample S in a direction perpendicular thereto in accordance with the conventional image acquiring method, the pattern of the surface of the sample S is displayed on the central portion of the display screen of the monitor 86. In this preferred embodiment, since the electron beams 6 are incident on the sample S at a predetermined slant angle, a slant image M1 is displayed on the screen so as to be shifted by Dev', which corresponds to an irradiation position shift quantity Dev, in the opposite direction to a direction in which the irradiation position is shifted from the center of the monitor screen.

The control computer 2 calculates an irradiation position shift quantity of the electron beams 6 using an input signal which is to be inputted to the slant observing deflection control part 62, and data on a deflection angle and energy of the electron beams 6, as parameters, and supplies the calculated results to the image processing control part 88. On the basis of the calculated results, the image processing control part 88 supplies a control signal for image correction to the image processing part 84. Then, the image processing part 84 excessively incorporates an image so as to include Dev' corresponding to the irradiation position shift as shown in the upper portion of FIG. 11C, and then, incorporates an image again at a position, at which the shift quantity Dev' is shifted, as shown by the arrow in the left direction in this figure. Thus, as shown in the lower portion of FIG. 11C, the shift quantity is corrected, so that a slant image M2 at the target position is observed at the center of the screen. Furthermore, the correction using the image processing should not be limited to the above-described method. For example, the image may be cut by the shift quantity due to the slant deflection and may be displayed in a smaller region than the usual region on the screen.

(7) Seventh Preferred Embodiment

Referring to the accompanying drawing, the seventh preferred embodiment of a charged particle beam system according to the present invention will be described below.

Figure 12:
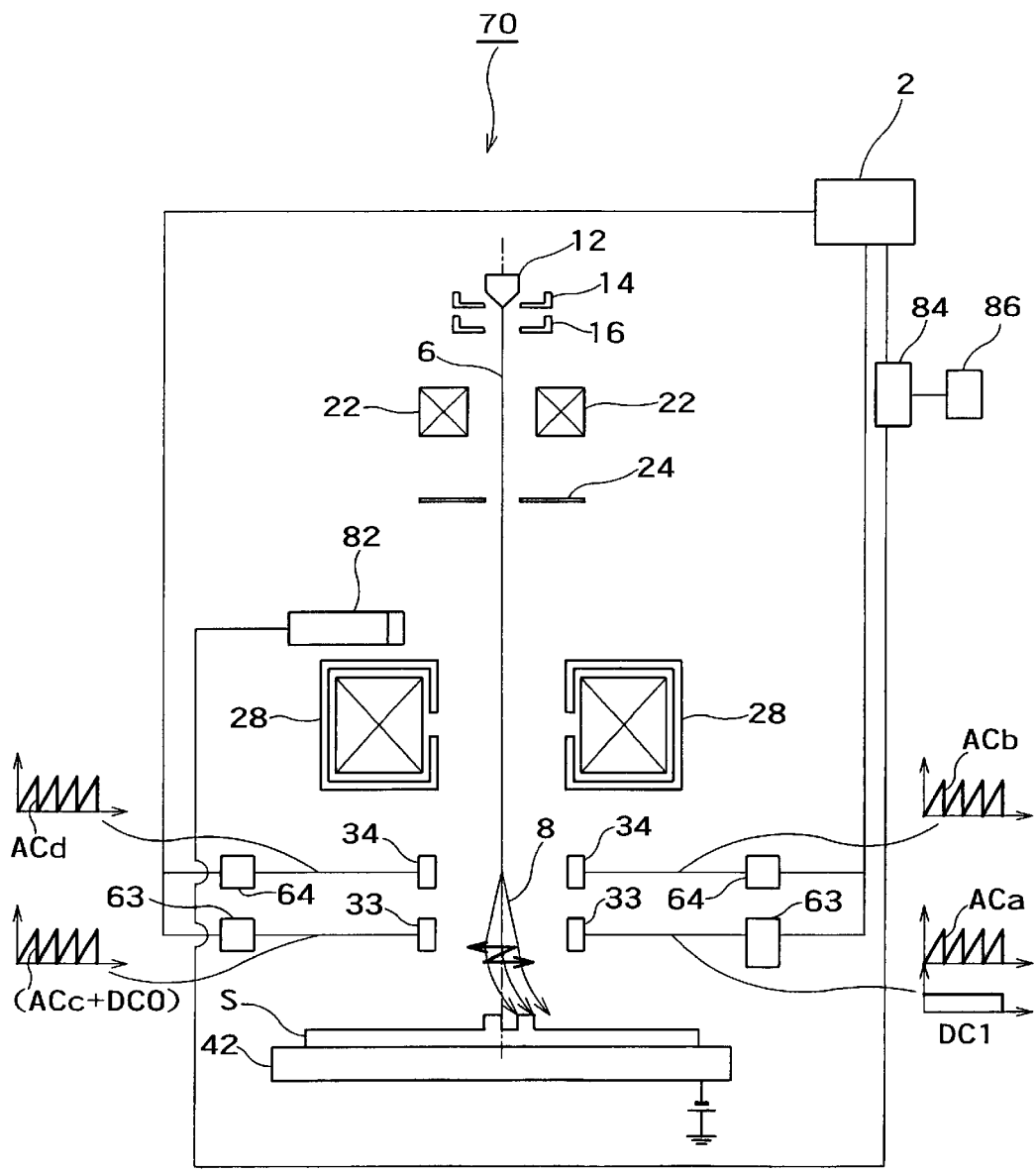
FIG. 12 is a schematic diagram showing the seventh preferred embodiment of a charged particle beam system according to the present invention.

FIG. 12 is a schematic diagram showing the construction of a charged particle beam system 70 in this preferred embodiment. As can be seen from the comparison with the charged particle beam system shown in FIG. 1, the charged particle beam system 70 further comprises two stages of slant observing deflecting devices 33, 34 and slant observing deflection control parts 63, 64, which are provided between the objective lens 28 and the sample S substituted for the scanning deflecting device and scanning deflection control part between the condenser lens 22 and the objective lens 28. The slant observing deflecting devices 33 and 34 substantially have the same construction as that of the above described slant observing deflecting part 32. Other constructions of the charged particle beam system 70 are substantially the same as those of the charged particle beam system 10 shown in FIG. 1.

This preferred embodiment is characterized in that the scanning and slant deflection of the electron beams 6 are simultaneously carried out by the two stages of slant observing deflecting devices 33 and 34. This will be described in detail below.

The electron beams 6 produced by the electron gun part to pass through the condenser lens 22 are focused by the objective lens 28 so as to form an image on the top face of the sample S. The slant observing deflecting devices 33 and 34 arranged between the objective lens 28 and the sample S are connected to the slant observing deflection control part 63 and 64, respectively. The slant observing deflection control part 64 in the upper stage (on the side of the objective lens 28) sets scanning AC voltage components ACb and ACd on the basis of a command signal from the control computer 2 as shown in the respective waveform illustrations on both sides of FIG. 12, and applies the set scanning AC voltage components ACb and ACd to the slant observing deflecting device 34 in the upper stage. On the other hand, the slant observing deflection control part 63 in the lower stage (on the side of the sample) sets voltages, which are obtained by adding slanting DC components DC1 and DC0 (=0) to scanning AC voltage components ACa and ACc on the basis of a command signal from the control computer 2 as shown in the waveform illustrations of the figure, and applies the set voltages to the slant observing deflecting device 34. Thus, the scanning deflection and slant observing deflection of the electron beams 6 can be simultaneously controlled. Furthermore, at this time, as the scanning AC components, signals of different levels are inputted to the facing electrodes in the respective slant observing deflecting devices 33 and 34, so that the deflection angle and deflection direction are controlled.

(8) Eighth Preferred Embodiment

Referring to the accompanying drawing, the eighth preferred embodiment of a charged particle beam system according to the present invention will be described below.

Figure 13:
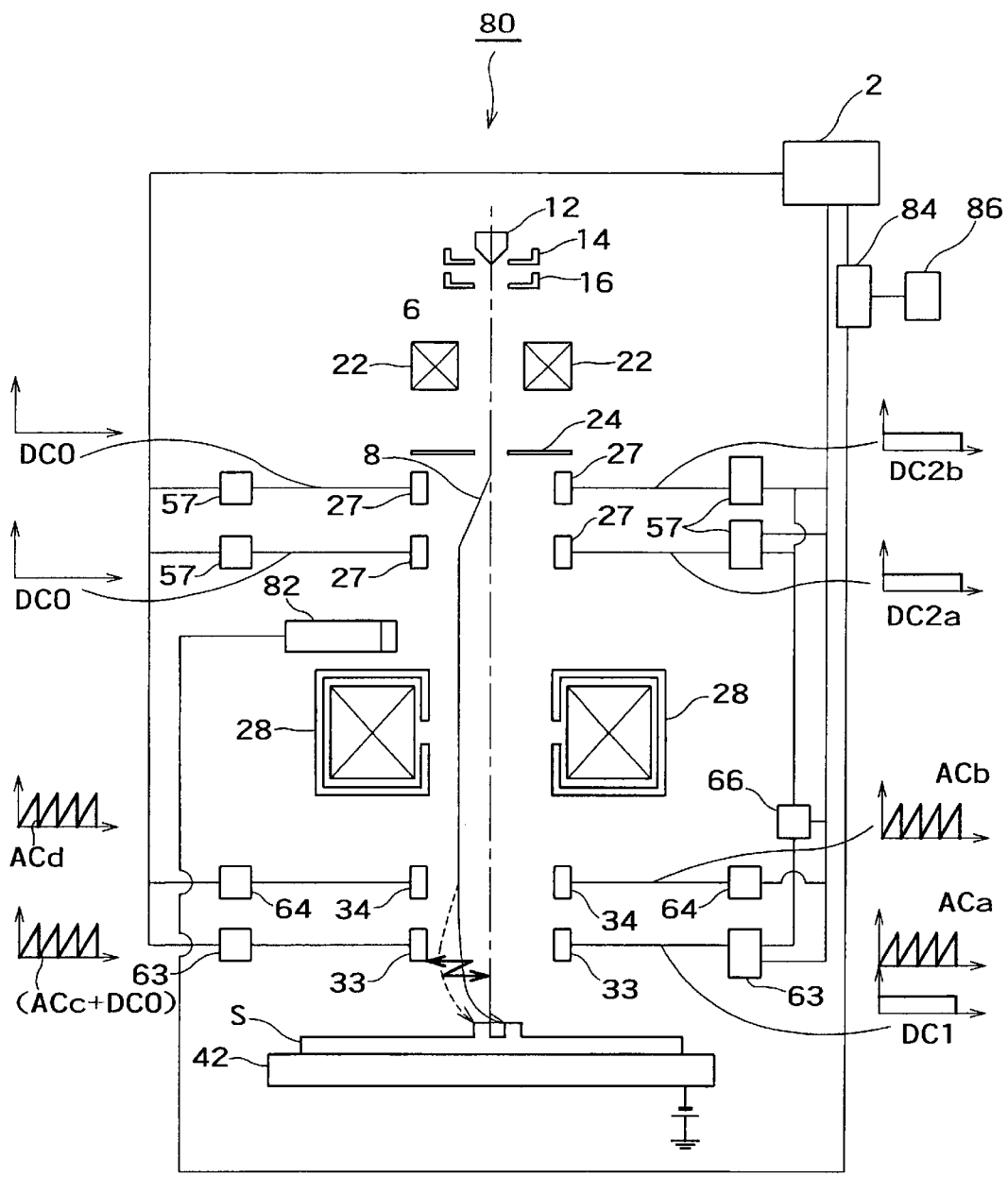
FIG. 13 is a schematic diagram showing the eighth preferred embodiment of a charged particle beam system according to the present invention.

FIG. 13 is a schematic diagram showing the construction of a charged particle beam system 80 in this preferred embodiment. As can be seen from the comparison with the charged particle beam system 70 shown in FIG. 12, the charged particle beam system 80 further comprises two stages of correction deflecting devices 27 provided above the objective lens 28, correction deflection control parts 57 connected to the correction deflecting devices 27, respectively, and a correction deflection calculating part 66. The correction deflection calculating part 66 is connected to the control computer 2, and to all of the slant observing deflection control part 63 in the lower stage and the correction deflection control parts 57. Other constructions of the charged particle beam system 80 are substantially the same as those of the charged particle beam system 70 shown in FIG. 12.

This preferred embodiment is characterized in that the scanning deflection and slant observing deflection of the electron beams 6 are simultaneously carried out by the slant observing deflecting device 33 and the slant observing deflection control part 63, and that the irradiation position shift of the electron beams 6 due to slant is corrected by the correction deflection calculating part 66, the correction deflecting device 27 and the correction deflection control part 57. The procedure for correcting the irradiation position shift using the charged particle beam system 80 will be described below.

First, the control computer 2 supplies data on a deflection angle and energy of the electron beams 6 to the correction deflection calculating part 66. The slant observing deflection control parts 63 and 64 also supply input signals, which are to be inputted to the slant observing deflecting devices 33 and 34 respectively, to the correction deflection calculating part 66. The correction deflection calculating part 66 uses these data as correcting parameters to calculate an irradiation position shift quantity of the electron beams 6. On the basis of the calculated results, the correction reflection calculating part 66 supplies a control signal for irradiation position shift correction to the correction reflection control part 57. On the basis of this control signal, the correction reflection control part 57 sets DC current components DC2$a$, DC2$b$, DC0 (=0) and DC0 (=0) capable of correcting the irradiation position shift and applies the current components to the corresponding electrodes of the correction deflecting device 27 respectively. In the embodiment of FIG. 13, the current components DC2$a$ and DC2$b$ are applied to the right electrodes of the correction deflecting device 27. Thus, the trajectories of the electron beams 6 are shifted in a direction in which the irradiation position shift is corrected by the correction deflecting device 27. As a result, it is possible to avoid the shift in the observation region due to deflection.

(9) Ninth Preferred Embodiment

Referring to the accompanying drawing, the ninth preferred embodiment of a charged particle beam system according to the present invention will be described below.

Figure 14:
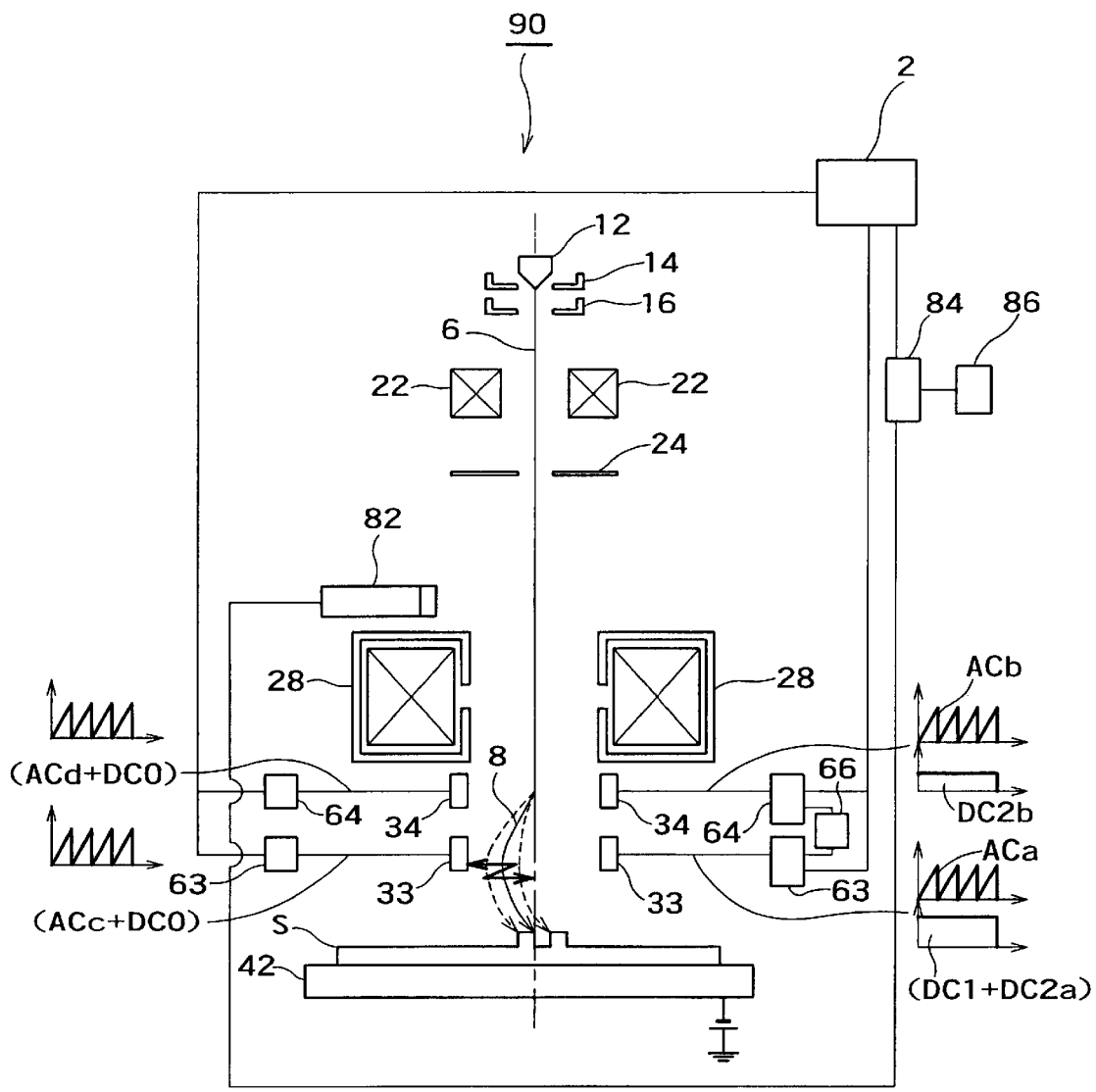
FIG. 14 is a schematic diagram showing the ninth preferred embodiment of a charged particle beam system according to the present invention.

FIG. 14 is a schematic diagram showing the construction of a charged particle beam system in the ninth preferred embodiment according to the invention. As can be seen from the comparison with the charged particle beam system 70 shown in FIG. 12, the charged particle beam system 90 in this preferred embodiment further comprises a correction deflection calculating part 66 connected to two stages of slant observing deflection control parts 63 and 64. Other constructions of the charged particle beam system 90 are substantially the same as those of the charged particle beam system 70 shown in FIG. 12.

This preferred embodiment is characterized in that the scanning deflection and slant observing deflection of the electron beams 6 and the correction of the irradiation position shift of the electron beams 6 due to slant are simultaneously carried out by the slant observing deflecting devices 33, 34 and the slant observing deflection control parts 63, 64. The procedure for correcting the irradiation position shift using the charged particle beam system 90 will be described below.

The correction deflection calculating part 66 receives a signal of a slanting DC component DC1, which is fed back from the lower-stage slant observing deflection control part 63, to calculates DC components DC2$a$ through DC2$d$ for correcting an irradiation position shift, supplies a control signal for causing the DC components DC2$a$ and DC2$c$ to the lower-stage slant observing deflection control part 63 and supplies a control signal for causing the DC components DC2$b$ and DC2$d$ to the upper-stage slant observing deflection control part 64. Thus, in the embodiment of FIG. 14, the DC components DC2a and DC2b are applied to the right electrodes of the slant observing deflecting devices 33 and 34 respectively. In the embodiment of this figure, the DC components DC2c and DC2d are DC0 (=0). The respective electron beams 6 pass through the objective lens 28 to pass through the upper-stage slant observing deflecting device 34 and lower-stage slant observing deflecting device 33 which are provided between the objective lens 28 and the sample S. A signal obtained by synthesizing three components of a scanning AC component ACa, the slanting DC component DC1 and the correcting DC component DC2a, which is fed back from the correction deflection calculating part 66, is set by the lower-stage slant observing deflection control part 63 to be inputted to one of the electrodes 144 of the lower-stage slant observing deflecting device 33 (the right electrode in the embodiment of FIG. 14). On the other hand, a signal obtained by synthesizing two components of a scanning AC component ACb and the correcting DC component DC2b is set by the upper-stage slant observing deflection control part 64 to be inputted to a corresponding one of the electrodes 144 of the upper-stage slant observing deflecting device 34 (the right electrode in the embodiment of FIG. 14). By thus setting and inputting the signals to the respective deflecting devices 33 and 34, the scanning deflection and slant observing deflection of the electron beams 6, and the correction of the irradiation position shift can be simultaneously controlled. At this time, as the scanning AC component Ac, the signals having the same level are inputted to the facing electrodes in the deflecting device. On the other hand, as the slant observing DC component DC, the signals having different levels are inputted to the facing electrodes in the deflecting device. Thus, the deflection angle and the deflection direction are controlled. In order to correct the irradiation position shift, although DC components having different levels are inputted to the facing electrodes in the deflecting device similar to the slant observing DC component, it is required that the trajectories of the electrode beams 6 are not bent in the scanning deflection.

While some preferred embodiments of the present invention have been described, the present invention should not be limited to the above-described embodiments, but the invention can be embodied in various ways without departing from the scope of the invention. While the irradiation position shift quantity has been calculated by the correction deflection calculating part in the above described second, third, eighth and ninth preferred embodiments, the irradiation position shift quantity may be calculated by the control computer similar to the fifth and sixth preferred embodiments. While the electron beams have been used as charged particle beams, ion beams due to ions other than electrons may be used.

What is claimed is:

1. A charged particle beam system comprising:
    a charged particle beam emitting device for generating a charged particle beam and for irradiating a sample to be inspected with said charged particle beam;
    a stage for supporting the sample thereon;
    a condenser lens for condensing said charged particle beam which enters from said charged particle beam emitting device along a beam axis of said charged particle beam, the beam axis being substantially perpendicular to a surface of said stage on which the sample is supported;
    a scanning deflecting device for deflecting said charged particle beam to scan said charged particle beam on the sample;
    an objective lens for focusing said charged particle beam on the surface of the sample;
    a slant observing deflecting device, arranged between said objective lens and the sample, for generating a nonuniform magnetic or a nonuniform electric field which deflects said charged particle beam at an arbitrary slant angle from the beam axis so that the trajectory of said charged particle beam is bent, said charged particle beam traveling along the bent trajectory to be obliquely incident on the sample;
    a charged particle detector for detecting a secondary charged particle and/or a reflected charged particle which are generated from the sample irradiated with said charged particle beam; and
    a control part for controlling said slant angle.

2. A charged particle beam system according to claim 1, wherein said slant observing deflecting device is an electrostatic deflecting device, and said control part controls the electrostatic deflecting device so that the nonuniform electric field is generated at a position at which said charged particle beam is going out of said slant observing deflecting device or in a region in the vicinity of the position.

3. A charged particle beam system according to claim 2, wherein the electrostatic deflecting device includes an insulator which is provided between said objective lens and the sample and on which a metal film is deposited, and the metal film constitutes an electrode of the electrostatic deflecting device.

4. A charged particle beam system according to claim 3, which further comprises an shielding electrode, incorporated in the electrostatic deflecting device, for shielding said objective lens from the electric field which is generated by the electrostatic deflecting device.

5. A charged particle beam system according to claim 3, wherein said control part includes an irradiation position shift correcting part for correcting an irradiation position shift caused by said charged particle beam which travels along the bent trajectory to be obliquely incident on the sample.

6. A charged particle beam system according to claim 5, wherein said irradiation position shift correcting part has:
    an irradiation position shift quantity calculating part for calculating a magnitude and a direction of the irradiation position shift on the basis of the slant angle; and
    a scanning deflection control part for controlling said scanning deflecting device on the basis of the calculated result of the irradiation position shift quantity calculating part to shift the trajectory of said charged particle beam by a distance according to the magnitude of the irradiation position shift in the opposite direction to the direction of the irradiation position shift.

7. A charged particle beam system according to claim 6, wherein said irradiation position shift correcting part further has an objective lens correction control part for controlling said objective lens on the basis of the calculated result of said irradiation position shift quantity calculating part to move said objective lens so that the trajectory of said charged particle beam shifted by the scanning deflecting control part passes through the center of s aid objective lens.

8. A charged particle beam system according to claim 7, wherein the objective lens correction control part electromagnetically moves said objective lens by shifting an electromagnetic field which is generated by said objective lens.

9. A charged particle beam system according to claim 7, which further comprises a movable lens supporting body for supporting said objective lens, wherein the objective lens correction control part mechanically moves said objective lens by moving said lens supporting body.

10. A charged particle beam system according to claim 5, wherein said stage being movable on a plane which is substantially perpendicular to the beam axis of said charged particle beam, the irradiation position shift correcting part has an irradiation position shift quantity calculating part for calculating a magnitude and a direction of the irradiation position shift on the basis of the slant angle, and a stage control part for moving said stage by a distance according to the magnitude of the irradiation position shift in the direction of the calculated irradiation position.

11. A charged particle beam system according to claim 5, which further comprises an image processing part for converting said secondary charged particle and/or said reflected charged particle into image data, and a display for displaying the image data as a charged particle beam image, said secondary charged particle and/or said reflected charged particle being detected by said charged particle detector, wherein the irradiation position shift correcting part has an irradiation position shift quantity calculating part for calculating a magnitude and a direction of the irradiation position shift on the basis of the slant angle, and an image correcting part for controlling the image processing part so that the charged particle beam image is displayed at a desired position on the display on the basis of the calculated results.

12. A charged particle beam system comprising:
   a charged particle beam emitting device for generating a charged particle beam and for irradiating a sample to be inspected with said charged particle beam;
   a stage for supporting the sample thereon;
   a condenser lens for condensing said charged particle beam which enters from said charged particle beam emitting device along a beam axis of said charged particle beam, the beam axis being substantially perpendicular to a surface of said stage on which the sample is supported;
   an objective lens for focusing said charged particle beam on the surface of the sample;
   a scanning/slant observing deflecting device, arranged between said objective lens and the sample, for generating a scanning magnetic field or a scanning electric field for scanning the sample with said charged particle beam and for generating an nonuniform magnetic field or a nonuniform electric field which deflects said charged particle beam at an arbitrary slant angle from the beam axis so that the trajectory of said charged particle beam is bent, said charged particle beam traveling along the bent trajectory to be obliquely incident on the sample;
   a charged particle detector for detecting a secondary charged particle and/or a reflected charged particle which are generated from the sample irradiated with said charged particle beam; and
   a control part for controlling the slant angle.

13. A charged particle beam system according to claim 12, which further comprises:
   an irradiation position shift quantity calculating part for calculating a magnitude and a direction of an irradiation position shift caused by said charged particle beam which travels along the bent trajectory to be obliquely incident on the sample, on the basis of the slant angle; and
   an irradiation position shift correcting part for controlling said scanning/slant a observing deflecting device to correct said irradiation position shift on the basis of the calculated result of said irradiation position shift quantity calculating part.

14. A charged particle beam system according to claim 13, which comprises a correction deflecting device, arranged between said condenser lens and said objective lens, for shifting the trajectory of said charged particle beam by a distance according to the magnitude of the position shift in the opposite direction to the direction of the position shift on the basis of the calculated results of said irradiation position shift quantity calculating part to correct the irradiation position shift, said correction deflecting device constituting an irradiation position shift correcting part.

15. A pattern slant observing method using a charged particle beam system which comprises a charged particle beam source, a charged particle beam optical system, a stage for supporting a sample on which a pattern is formed, and a charged particle detector, said charged particle beam optical system including a scanning deflecting device and an objective lens, said pattern slant observing method comprising:
   an irradiation step of emitting a charged particle beam from said charged particle beam source and of irradiating the sample with said charged particle beam, said charged particle beam traveling along a beam axis thereof to enter said charged particle beam system, the beam axis being substantially perpendicular to a surface of said stage on which the sample is supported;
   a scanning step of deflecting said charged particle beam by said scanning deflecting device to scan said charged particle beam on the sample;
   a focusing step of focusing said charged particle beam on the surface of the sample by said objective lens;
   a slant incident step of forming a nonuniform electric field or a nonuniform magnetic field at a position at which said charged particle beam leaves said charged particle beam optical system or in a region in the vicinity of the position and of deflecting said charged particle beam by said nonuniform electric field or a nonuniform magnetic field so that the trajectory of said focused charge particle beam is bent at an arbitrary slant angle from the beam axis of said charged particle beam and said charged particle beam travels along the bent trajectory to be obliquely incident on the sample;
   a detection step of detecting a secondary charged particle and/or a reflected charged particle which are generated from the sample by irradiation with said charged particle beam; and
   an image data acquiring step of acquiring image data, which are to be a slant image of the pattern, on the basis of the secondary charged particle and/or the reflected charged particle.

16. A pattern slant observing method according to claim 15, which further comprises an electromagnetic shielding step of preventing said nonuniform electric or said nonuniform magnetic field from entering a region which is closer to said charged particle beam source than a region in which the trajectory of said charged particle beam is bent at the slant angle from the beam axis.

17. A pattern slant observing method according to claim 16, which further comprises an irradiation position shift quantity calculating step of calculating a magnitude and a direction of an irradiation position shift caused by said charged particle beam which travels along the bent trajectory to be obliquely incident on the sample on the basis of said slant angle, wherein said scanning step includes a step of shifting the trajectory of said charged particle beam by a distance according to the magnitude of the irradiation position shift in the opposite direction to the direction of the irradiation position shift on the basis of the calculated results at said irradiation position shift quantity calculating step.

18. A pattern slant observing method according to claim 17, which further comprises a step of moving said objective lens on a plane substantially perpendicular to the beam axis of said charged particle beam in accordance with the shift of the trajectory of said charged particle beam so that the shifted charged particle beam passes through the center of said objective lens.

19. A pattern slant observing method according to claim 16, wherein said stage of said charged particle beam system is movable on a plane substantially perpendicular to the beam axis of said charged particle beam, and the pattern slant observing method further comprises:

an irradiation position shift quantity calculating step of calculating a magnitude and a direction of an irradiation position shift caused by said charged particle beam which travels along the bent trajectory to be obliquely incident on the sample, on the basis of said slant angle; and a step of moving said stage by a distance according to said irradiation position shift quantity in the direction of the irradiation position shift on the basis of the calculated results at said irradiation position shift quantity calculating step.

20. A pattern slant observing method according to claim 16, wherein said charged particle beam system further comprises a display for displaying the image data as a charged particle beam image, and the pattern slant observing method further comprises:

an irradiation position shift quantity calculating step of calculating a magnitude and a direction of an irradiation position shift caused by said charged particle beam which travels along the bent trajectory to be obliquely incident on the sample, on the basis of said slant angle; and an image correcting step of correcting the image data so that the charged particle beam image is displayed at a desired position on said display on the basis of the calculated results.

21. A pattern slant observing method according to claim 16, wherein said scanning step is carried out simultaneously with said slant incident step at a position, at which said charged particle beam leaves said charged particle beam optical system, or in a region in the vicinity of the position.

22. A pattern slant observing method according to claim 21, which further comprises:

an irradiation position shift quantity calculating step of calculating a magnitude and a direction of an irradiation position shift caused by said charged particle beam which travels along the bent trajectory to be obliquely incident on the sample, on the basis of the slant angle; and a correction deflecting step of shifting the trajectory of said charged particle beam by a distance according to the magnitude of said irradiation position shift in the opposite direction to the direction of the irradiation position shift, at a position, at which said charged particle beam leaves said charged particle beam optical system, or in a region in the vicinity of the position, on the basis of the calculated results at said irradiation position shift quantity calculating step.

23. A pattern slant observing method according to claim 16, which further comprises:

an irradiation position shift quantity calculating step of calculating a magnitude and a direction of an irradiation position shift caused by said charged particle beam which travels along the bent trajectory to be obliquely incident on the sample, on the basis of the slant angle; and a correction deflecting step of shifting the trajectory of said charged particle beam by a distance according to the magnitude of the irradiation position shift in the opposite direction to the direction of the irradiation position shift, in a region which is closer to said charged particle beam source than said objective lens in said charged particle beam optical system, on the basis of the calculated results at said irradiation position shift quantity calculating step.

* * * * *